US009340501B2

(12) United States Patent
Li et al.

(10) Patent No.: US 9,340,501 B2
(45) Date of Patent: May 17, 2016

(54) MARINOPYRROLE DERIVATIVES AS ANTICANCER AGENTS

(71) Applicant: H. LEE MOFFITT CANCER CENTER AND RESEARCH INSTITUTE, INC., Tampa, FL (US)

(72) Inventors: Rongshi Li, Tampa, FL (US); Said M. Sebti, Tampa, FL (US); Yan Liu, Tampa, FL (US)

(73) Assignee: H. Lee Moffitt Cancer Center and Research Institute, Inc., Tampa, FL (US)

( * ) Notice: Subject to any disclaimer, the term of this patent is extended or adjusted under 35 U.S.C. 154(b) by 0 days.

(21) Appl. No.: 14/394,902

(22) PCT Filed: Feb. 1, 2013

(86) PCT No.: PCT/US2013/024424
§ 371 (c)(1),
(2) Date: Oct. 16, 2014

(87) PCT Pub. No.: WO2013/158197
PCT Pub. Date: Oct. 24, 2013

(65) Prior Publication Data
US 2015/0080632 A1 Mar. 19, 2015

Related U.S. Application Data

(60) Provisional application No. 61/624,792, filed on Apr. 16, 2012, provisional application No. 61/624,758, filed on Apr. 16, 2012.

(51) Int. Cl.
| | |
|---|---|
| A61K 31/4025 | (2006.01) |
| C07D 403/04 | (2006.01) |
| C07D 207/34 | (2006.01) |
| A61K 45/06 | (2006.01) |
| A61N 5/10 | (2006.01) |
| C07D 207/335 | (2006.01) |

(52) U.S. Cl.
CPC .......... *C07D 207/34* (2013.01); *A61K 31/4025* (2013.01); *A61K 45/06* (2013.01); *A61N 5/10* (2013.01); *C07D 207/335* (2013.01); *C07D 403/04* (2013.01); *A61N 2005/1098* (2013.01)

(58) Field of Classification Search
None
See application file for complete search history.

(56) References Cited

U.S. PATENT DOCUMENTS

| | | | |
|---|---|---|---|
| 4,559,157 A | 12/1985 | Smith et al. | |
| 4,608,392 A | 8/1986 | Jacquet et al. | |
| 4,820,508 A | 4/1989 | Wortzman | |
| 4,992,478 A | 2/1991 | Geria | |
| 6,468,953 B1 | 10/2002 | Hitchems et al. | |

FOREIGN PATENT DOCUMENTS

| | | |
|---|---|---|
| WO | 2011/103788 | 2/2011 |
| WO | 2014/116634 | 7/2014 |

OTHER PUBLICATIONS

Hughes, et al., J. Org. Chem., 75:3240 (Apr. 20, 2010).*
Cheng, et al., J. Comb. Chem., 12:541 (Apr. 29, 2010).*
Nicolaou, et al., Tet. Lett., 52:2041 (Oct. 11, 2010).*
Acoca, S., et al., "Molecular dynamics study of small molecule inhibitors of the Bcl-2 family," Proteins, vol. 79, 2011, pp. 2624-2636.
Albershardt, T.C., et al., "Multiple BH3 Mimetics Antagonize Antiapoptotic MCL1Protein by Inducing the Endoplasmic Reticulum Stress Response and Up-regulating BH3-only Protein NOXA," The Journal of Biological Chemistry, vol. 286, No. 28, 2011, pp. 24882-24895.
Beroukhim, R., et al., "The landscape of somatic copy-number alteration across human cancers," Nature, vol. 463, 2010, pp. 899-905.
Bhat, U.G., et al., "ARC Synergizes with ABT-737 to Induce Apoptosis in Human Cancer Cells," Molecular Cancer Therapeutics, vol. 9, 2010, pp. 1688-1696.
Butler, K.V., et al., "Rational Design and Simple Chemistry Yield a Superior, Neuroprotective HDAC6 Inhibitor, Tubastatin A," Journal of the American Chemical Society, vol. 132, 2010, pp. 10842-10846.
Chen, S., et al., "Mcl-1 Down-regulation Potentiates ABT-737 Lethality by Cooperatively Inducing Bak Activation and Bax Translocation," Cancer Research, vol. 67, 2007, pp. 782-791.
Czabotar, P.E., et al., "Structural insights into the degradation of Mcl-1induced by BH3 domains," Proceedings of the National Academy of Sciences, vol. 104, 2007, pp. 6217-6222.
Day, C.L., et al., "Structure of the BH3 Domains from the p53-Inducible BH3-Only Proteins Noxa and Puma in Complex with Mcl-1," Journal of Molecular Biology, vol. 380, 2008, pp. 958-971.
Domina, A.M., et al., "MCL1 is phosphorylated in the PEST region and stabilized upon ERK activation in viable cells, and at additional sites with cytotoxic okadaic acid or taxol," Oncogene, vol. 23, 2004, pp. 5301-5315.
Eldridge, M.D., et al., "Empirical scoring functions: I. The development of a fast empirical scoring function to estimate the binding affinity of ligands in receptor complexes," Journal of Computer-Aided Molecular Design, vol. 11, 1997, pp. 425-445.
Facchetti, F., et al., "Modulation of pro- and anti-apoptotic factors in human melanoma cells exposed to histone deacetylase inhibitors," Apoptosis, vol. 9, 2004, pp. 573-582.
Fournel, M., et al., "MGCD0103, A novel isotype-selective histone deacetylase inhibitor, has broad spectrum antitumor activity in vitro and in vivo," Molecular Cancer Therapeutics, vol. 7, 2008, pp. 759-768.
Friesner, R.A., et al., "Glide: A New Approach for Rapid, Accurate Docking and Scoring. I. Method and assessment of Docking Accuracy," Journal of Medicinal Chemistry, vol. 47, 2004, pp. 1739-1749.
Furneaux, R.H., et al., "Improved Syntheses of 3H,5H-Pyrrolo [3,2-d] pyrimidines," The Journal of Organic Chemistry, vol. 64, 1999, pp. 8411-8412.
Gao, L., et al., "Cloning and Functional Characterization of HDAC11, a Novel Member of the Human Histone Deacetylase Family," The Journal of Biological Chemistry, vol. 277, No. 28, 2002, pp. 25748-25755.

(Continued)

*Primary Examiner* — Michael Barker
(74) *Attorney, Agent, or Firm* — Meunier Carlin & Curfman LLC

(57) ABSTRACT

Marinopyrrole derivatives and methods for their synthesis and use are described herein. The methods of using the compounds include treating and preventing cancer.

19 Claims, 2 Drawing Sheets

(56) References Cited

OTHER PUBLICATIONS

Gomez-Bougie, P., et al., "Noxa controls Mule-dependent Mcl-1 ubiquitination through the regulation of the Mcl-1/USP9X interaction," Biochemical and Biophysical Research Communications, vol. 413, 2011, pp. 460-464.

Guo, D., et al., "Efficient Iron-Catalyzed N-Arylation of Aryl Halides with Amines," Organic Letters, vol. 10, No. 20, 2008, pp. 4513-4516.

Haste, N.M., et al., Pharmacological Properties of the Marine Natural Product Marinopyrrole A against Methicillin-Resistant *Staphylococcus aureus*, Antimicrobial Agents and Chemotherapy, vol. 55, No. 7, 2011, pp. 3305-3312.

Hikita, H., et al., "The Bcl-xL Inhibitor, ABT-737, Efficiently Induces Apoptosis and Suppresses Growth of Hepatoma Cells in Combination with Sorafenib," Hepatology, vol. 52, No. 4, 2010, pp. 1310-1321.

Hu, X., et al., "Bcl-$X_L$-templated assembly of its own protein-protein interaction modulator from fragments decorated with thio acids and sulfonyl azides," Journal of the American Chemical Society, vol. 130, No. 42, 2008, pp. 13820-13821.

Hughes, C.C., et al., "Marinopyrrole A Target Elucidation by Acyl Dye Transfer," Journal of the American Chemical Society, vol. 131, No. 34, 2009, pp. 12094-12096.

Hughes, C.C., et al., The Marinopyrroles, Antibiotics of an Unprecedented Structure Class from a Marine *Streptomyces* sp., Organic Letters, vol. 10, No. 4, 2008, pp. 629-631.

Ji, M., et al., "Simultaneous targeting of *MCL1* and *ABCB1* as a novel strategy to overcome drug resistance in human leukaemia," British Journal of Haematology, vol. 145, 2009, pp. 648-656.

Jorgensen, W.L., et al., "Development and Testing of the OPLS All-Atom Force Field on Conformational Energetics and Properties of Organic Liquids," Journal of the American Chemical Society, vol. 118, 1996, pp. 11225-11236.

Kalin, K.H., et al., "Second-Generation Histone Deacetylase 6 Inhibitors Enhance the Immunosuppressive Effects of Foxp3+ T-Regulatory Cells," Journal of Medicinal Chemistry, vol. 55, 2012, pp. 639-651.

Kanakis, A.A., et al., "Total Synthesis of (±)—Marinopyrrole A via Copper-Mediated N-Arylation," Organic Letters, vol. 12, No. 21, 2010, pp. 4872-4875.

Kazi, A., et al., "The BH3 α-Helical Mimic BH3-M6 Disrupts Bcl-$X_L$, Bcl-2, and MCL-1 Protein-Protein Interactions with Bax, Bak, Bad, or Bim and Induces Apoptosis in a Bax- and Bim-dependent Manner," The Journal of Biological Chemistry, vol. 286, No. 11, 2011, pp. 9382-9392.

Kelly, W.K., et al., "Drug Insight: histone deacetylase inhibitors—development of the new targeted anticancer agent suberoylanilide hydroxamic acid," Nature Clinical Practice Oncology, vol. 2, No. 3, 2005, pp. 150-157.

Konopleva, M., et al. "Mechanisms of apoptosis sensitivity and resistance to the BH3 mimetic ABT-737 in acute myeloid leukemia," Cancer Cell, vol. 10, 2006, pp. 375-388.

Krajewska, M., et al., Immunohistochemical Analysis of in Vivo Patterns of Expression of CPP32 (Caspase-3), a Cell Death Protease, Cancer Research, vol. 57, 1997, pp. 1605-1613.

Krajewski, S., et al., "Immunohistochemical Analysis of Mcl-1 and Bcl-2 Proteins in Normal and Neoplastic Lymph Nodes," American Journal of Pathology, vol. 145, No. 3, 1994, pp. 515-525.

Kwong, F.Y., et al, "Copper-catalyzed coupling of alkylamines and aryl iodides: An efficient system even in an air atmosphere," Organic Letters, vol. 4, 2002, pp. 581-584.

Li, R., et al., "Design, synthesis and evaluation of marinopyrrole derivatives as selective inhibitors of Mcl-1 binding to pro-apoptotic Bim and dual Mcl-1/Bcl-xL inhibitors," European Journal of Medicinal Chemistry, vol. 90, 2015, pp. 315-331.

Liao, A., et al., "Therapeutic efficacy of FTY720 in a rat model of NK-cell leukemia," Blood, vol. 118, No. 10, 2011, pp. 2793-2800.

Lin, X., et al., "'Seed' analysis of off-target siRNAs reveals an essential role of Mcl-1 in resistance to the small-molecule Bcl-2/Bcl-$X_L$ inhibitor ABT-737," Oncogene, vol. 26, 2007, pp. 3972-3979.

Maurer, U., et al., Glycogen Synthase Kinase-3 Regulates Mitochondrial Outer Membrane Permeabilization and Apoptosis by Destabilization of MCL-1, Molecular Cell, vol. 21, 2006, pp. 749-760.

Nguyen, M., et al., "Small molecule obatoclax (GX15-070) antagonizes MCL-1 and overcomes MCL-1-mediated resistance to apoptosis," Proceedings of the National Academy of Sciences, vol. 104, No. 49, 2007, pp. 19512-19517.

Okano, K., et al., "Synthesis of Secondary Arylamines through Copper-Mediated Intermolecular Aryl Amination," Organic Letters, vol. 5, No. 26, 2003, pp. 4987-4990.

Oltersdorf, T., et al., "An inhibitor of Bcl-2 family proteins induces regression of solid tumours," Nature, vol. 435, 2005, pp. 677-681.

Paremigiani, R.B., et al., "HDAC6 is a specific deacetylase of peroxiredoxins and is involved in redox regulation," Proceedings of the National Academy of Sciences, vol. 105, No. 28, 2008, pp. 9633-9638.

Quinn, B.A., et al., "Targeting Mcl-1 for the therapy of cancer," Expert Opinion on Investigational Drugs, vol. 20, No. 10, 2011, pp. 1397-1411.

Reed, J.C., et al., "BCL-2 Family Proteins: Regulators of Cell Death Involved in the Pathogenesis of Cancer and Resistance to Therapy," Journal of Cellular Biochemistry, vol. 60, 1996, pp. 23-32.

Reed, J.C., et al., Bcl-2 Family Proteins: Strategies for Overcoming Chemoresistance in Cancer, Advances in Pharmacology, vol. 41, 1997, pp. 501-532.

Rochais, C., et al., "Synthesis and biological evaluation of novel pyrrolopyrrolizinones as anticancer agents," Bioorganic & Medicinal Chemistry, vol. 14, 2006, pp. 8162-8175.

Santo, L., et al., "Preclinical activity, pharmacodynamic, and pharmacokinetic properties of a selective HDAC6 inhibitor, ACY-1215, in combination with bortezomib in multiple myeloma," Blood, vol. 119, 2012, pp. 2579-2589.

Sattler, M., et al., Structure of Bcl-$x_L$-Bak Peptide Complex: Recognition Between Regulators of Apoptosis, Science, vol. 275, 1997, pp. 983-986.

Stewart, M.L., et al., "The MCL-1 BH3 helix is an exclusive MCL-1 inhibitor and apoptosis sensitizer," Nature Chemical Biology, vol. 6, 2010, pp. 595-601.

Tahir, S.K., et al., "Influence of Bcl-2 Family Members on the Cellular Response of Small-Cell Lung Cancer Cell Lines to ABT-737," Cancer Research, vol. 67, 2007, pp. 1176-1183.

Tse, C., et al., "ABT-263: A Potent and Orally Bioavailable Bcl-2 Family Inhibitor," Cancer Research, vol. 68, No. 9, 2008, pp. 3421-3428.

van Delft, M.F., et al., "The BH3 mimetic ABT-737 targets selective Bcl-2 proteins and efficiently induces apoptosis via Bak/Bax if Mcl-1 is neutralized," Cancer Cell, vol. 10, 2006, pp. 389-399.

Vickers, C.J., et al., "Discovery of HDAC Inhibitors That Lack an Active Site $Zn^{2+}$-Binding Functional Group," ACS Medicinal Chemistry Letters, vol. 3, 2012, pp. 505-508.

Villagra, A., et al., "The histone deacetylase HDAC11 regulates the expression of interleukin 10 and immune tolerance," Nature Immunology, vol. 10, No. 1, 2009, pp. 92-100.

Vogler, M. et al., "Bcl-2 inhibitors: small molecules with a big impact on cancer therapy," Cell Death and Differentiation, vol. 16, 2009, pp. 360-367.

Wagner, J.M., et al., "Histone deacetylase (HDAC) inhibitors in recent clinical trials for cancer therapy," Clinical Epigenetics, vol. 1, 2010, pp. 117-136.

Wang, G-Q, et al., "A Role for Mitochondrial Bak in Apoptotic Response to Anticancer Drugs," The Journal of Biological Chemistry, vol. 276, 2001, pp. 34307-34317.

Wang, H., et al., "Histone Deacetylase Inhibitor LAQ824 Augments Inflammatory Responses in Macrophages through Transcriptional Regulation of IL-10," The Journal of Immunology, vol. 186, 2011, pp. 3986-3996.

Willis, S.N., et al., Proapoptotic Bak is sequestered by Mcl-1 and Bcl-xL, but not Bcl-2, until displaced by BH3-only proteins, Genes Dev 19:1294-1305, 2005.

Woods, N.T., et al., "Anoikis, Initiated by Mcl-1 Degradation and Bim Induction, is Deregulated during Oncogenesis," Cancer Research, vol. 67, No. 22, 2007, pp. 10744-10752.

(56) References Cited

OTHER PUBLICATIONS

Wuillème-Toumi, S., et al., "Reciprocal protection of Mcl-1 and Bim from ubiquitin-proteasome degradation," Biochemical and Biophysical Research Communications, vol. 361, 2007, pp. 865-869.

Yecies, D., et al., "Acquired resistance to ABT-737 in lymphoma cells that up-regulate MCL-1 and BFL-1," Blood, vol. 115, 2010, pp. 3304-3313.

Yip, K.W., et al., "Bcl-2 family proteins and cancer," Oncogene, 2008, vol. 27, pp. 6398-6406.

Zhang, Y., et al., "Mice Lacking Histone Deacetylase 6 Have Hyperacetylated Tubulin but Are Viable and Develop Normally," Molecular and Cellular Biology, vol. 28, 2008, pp. 1688-1701.

Zhou, N., et al., "Discovery of N-(2-Aminophenyl)-4-[4-pyridin-3-ylpyrimidin-2-ylamino)methyl]benzamide (MGCD0103), an Orally Active Histone Deacetylase Inhibitor," Journal of Medicinal Chemistry, vol. 51, 2008, pp. 4072-4075.

Zou, H., et al., "Characterization of the two catalytic domains in histone deacetylase 6," Biochemical and Biophysical Research Communications, vol. 341, 2006, pp. 45-50.

International Preliminary Report on Patentability and Written Opinion, dated Oct. 21, 2014, received in connection with International Patent Application No. PCT/US2013/024424.

International Search Report and Written Opinion, dated Jun. 2, 2013, received in connection with International Patent Application No. PCT/US2013/024424.

International Preliminary Report on Patentability and Written Opinion, dated Jul. 28, 2015, received in connection with International Patent Application No. PCT/US2014/012442.

International Search Report, dated Apr. 30, 2014, received in connection with International Patent Application No. PCT/US2014/012442.

* cited by examiner

MARINOPYRROLE DERIVATIVES AS ANTICANCER AGENTS

CROSS REFERENCE TO RELATED APPLICATIONS

This invention was made with government support under grant number CA118210, awarded by the National Institutes of Health. The government has certain rights in the invention.

STATEMENT REGARDING FEDERALLY FUNDED RESEARCH

This invention was made with government support under grant numbers CA118210, and GM090658 awarded by the National Institutes of Health and grant number MCB0939014 awarded by the National Science Foundation. The government has certain rights in the invention.

FIELD

The subject matter disclosed herein generally relates to marinopyrrole derivatives and methods of their preparation. Also, the subject matter described herein generally relates to methods of using the marinopyrrole derivatives described herein to treat and/or prevent cancer.

BACKGROUND

Apoptosis is the best-characterized mode of physiological cell death, which plays an essential role in the development and homeostasis of multicellular organisms. Apoptosis is executed by caspases, a family of cysteine proteases, whose activation is initiated via two major pathways: the death receptor (extrinsic) pathway and the mitochondrial (intrinsic) pathway. The activated caspases cleave a number of cellular proteins to generate many of the hallmark morphological features of apoptosis, including DNA fragmentation sand membrane blebbing.

The Bcl-2 family of proteins plays a pivotal role in apoptosis by regulating the mitochondrial outer membrane permeabilization (MOMP). MOMP results in the release of apoptogenic factors (e.g., cytochrome c and Smac) from the mitochondria into the cytosol where they directly promote caspase activation and subsequent cell death. Members of the Bcl-2 family contain up to four evolutionarily conserved domains called Bcl-2 homology (BH) domains 1 to 4 and can be classified into three groups based on their domain architecture and function in apoptosis: multidomain (BH1-4) anti-apoptotic Bcl-2 proteins (e.g., Bcl-2, Bcl-$X_L$ and Mcl-1), multidomain (BH1-3) pro-apoptotic Bcl-2 proteins (e.g., Bax and Bak), and BH3-only Bcl-2 proteins (e.g., Bad, Bid, Bim, Noxa and Puma). Many of the Bcl-2 family proteins can interact with each other to determine the cell fate. The three-dimensional structure reveal that the BH1-3 domains of anti-apoptotic Bcl-2 proteins form a hydrophobic surface groove to which the BH3 domains of pro-apoptotic Bcl-2 family members bind (Sattler er al., (1997) *Science* 275:983-986; Day et al., (2008) *J Mol Biol* 380:958-971). The multidomain pro-apoptotic Bcl-2 proteins Bax and Bak are two major effectors of MOMP, which homo-oligomerize and form pores in the mitochondrial outer membrane to induce MOMP upon apoptotic stimulation. The anti-apoptotic Bcl-2 proteins prevent MOMP by directly binding to both classes of pro-apoptotic Bcl-2 proteins. In contrast, the BH3-only proteins trigger Bax and Bak to induce MOMP. Based on their ability to interact with the multidomain anti- and pro-apoptotic Bcl-2 proteins, the BH3-only proteins are often further divided into two subgroups: direct activators and sensitizers/de-repressors. The direct activators, including Bid, Bim and Puma, are able to not only interact with and inhibit all the anti-apoptotic Bcl-2 proteins but also directly bind to and activate the effectors Bax and Bak. On the other hand, the sensitizers/de-repressors appear to function essentially as transdominant inhibitors by occupying the hydrophobic groove of anti-apoptotic Bcl-2 proteins, thereby displacing the direct activators to promote MOMP and preventing any future bindings of the direct activators or effectors to anti-apoptotic Bcl-2 proteins. Moreover, unlike the direct activators, the sensitizers/de-repressors are more selective in binding to the anti-apoptotic Bcl-2 members. For example, Bad binds and antagonizes Bcl-2 and Bcl-$X_L$ but not Mcl-1, whereas Noxa binds and antagonizes Mcl-1 but not Bcl-2 and Bcl-$X_L$. This observation indicates that the BH3-only proteins provide a fine control of MOMP in a Bax/Bak-dependent manner and opportunities to design specific inhibitors for each of the anti-apoptotic Bcl-2 family members.

The evasion of apoptosis is considered to be a hallmark of cancers and a cause of resistance to radiation and chemotherapies. Consistently, high levels of the anti-apoptotic Bcl-2 family proteins are associated with the pathogenesis of cancer and resistance to therapy (Reed et al., (1996) *J Cell Biochem* 60:23-32; Reed, (1997) *Adv Pharmacol* 41:501-532). A recent analysis of somatic copy-number alterations (SCNAs) showed that two anti-apoptotic Bcl-2 family genes (Bcl-$X_L$ and Mcl-1) undergo frequent somatic amplifications in multiple cancers and that cancer cells carrying Bcl-$X_L$ and Mcl-1 amplifications are dependent on the expression of these genes for survival (Beroukhim et al., (2010) *Nature* 463:899-905). Thus, Bcl-$X_L$ and Mcl-1 are very attractive targets for the development of anticancer agents.

Over the last few years, several small-molecule Bcl-2 inhibitors have been synthesized as BH3 mimetics and some of these molecules have entered clinical trials (Yip et al., (2008) *Oncogene* 27:6398-6406; Vogler et al., (2009) *Cell Death Difer* 16:360-367; Kazi et al., (2011) *J Biol Chem* 286:9382-9392). Although Bcl-2 and Bcl-$X_L$ have been the primary focus for the design of small-molecule inhibitors, recent studies have demonstrated that Mcl-1 also plays an important role for cancer cell survival and that it is necessary to neutralize both arms of the anti-apoptotic Bcl-2 family (Bcl-2/Bcl-$X_L$ and Mcl-1) for apoptosis to occur in many cell types (Willis et al., (2005) *Genes Dev* 19:1294-1305).

To date, the most potent and selective small-molecule Bcl-2 inhibitors are ABT-737 and its orally active analog ABT-263, which inhibit Bcl-2 and Bcl-$X_L$ at subnanomolar concentrations but only weakly target Mcl-1 (Tse et al., (2008) *Cancer Res* 68:3421-3428). Consequently, these agents generally lack efficacy in cancers with elevated Mcl-1 and in many instances this resistance can be overcome by downregulation of Mcl-1 (Id.; Oltersdorf et al., (2005) *Nature* 435:677-681; van Delft et al., (2006) *Cancer Cell* 10:389-399; Chen et al., (2007) *Cancer Res* 67, 782-791; Konopleva et al., (2006) *Cancer Cell* 10:375-388; Lin et al., (2007) *Oncogene* 26:3972-3979; Tahir et al., (2007) *Cancer Res* 67:1176-1183). Moreover, it has recently been shown that cancer cells can quickly acquire resistance to ABT-737 by upregulation of Mcl-1 (Yecies et al., (2009) *Blood* 233-304; Hikita et al., (2010) *Hepatology* 52:1310-1321). What are thus needed are compounds that specifically bind to Mcl-1 to overcome such resistance. Such compounds can be used to treat and/or prevent various cancers. The compositions and methods disclosed herein address these and other needs.

SUMMARY

In accordance with the purposes of the disclosed materials, compounds, compositions, kits, and methods, as embodied and broadly described herein, the disclosed subject matter relates to compositions, methods of making said compositions, and methods of using said compositions. More specifically, marinopyrrole derivatives for use as anticancer agents are provided herein. In specific aspects, the disclosed subject matter relates to anticancer agents. More specifically, the subject matter disclosed herein relates to marinopyrrole derivatives and their use in the treatment and prevention of cancer. Methods of making and using marinopyrrole derivatives are also disclosed herein.

Additional advantages will be set forth in part in the description that follows or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURES

The accompanying figures, which are incorporated in and constitute a part of this specification, illustrate several aspects described below.

Figure 1:
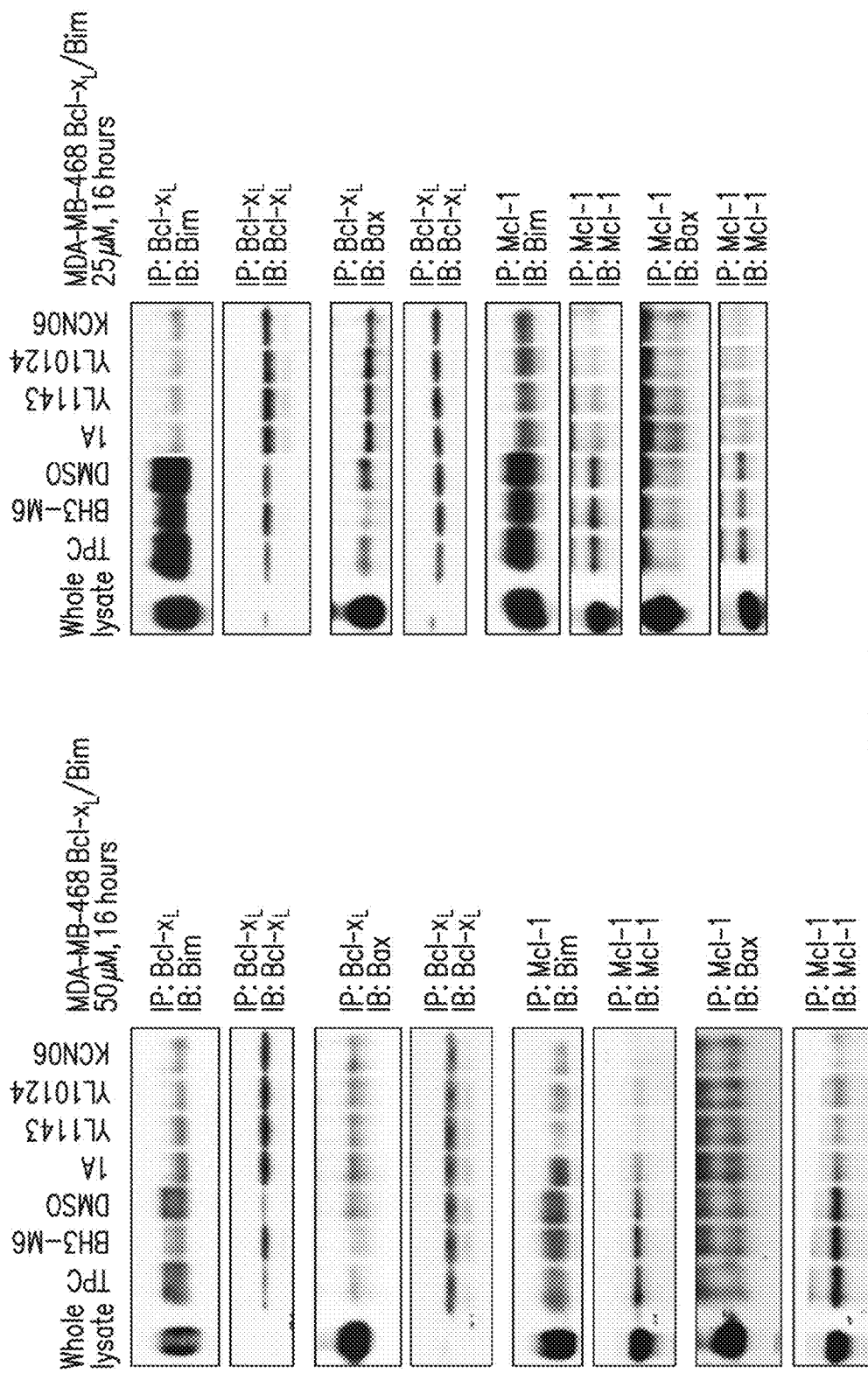
FIG. 1 shows marinopyrrole derivatives inhibit the binding of Bcl-xL to Bim and Mcl-1 to Bim at 50 and 25 μM after 16 hour treatment of MDA-MB-468 Bcl-xL/Bim cells.
Figure 2:
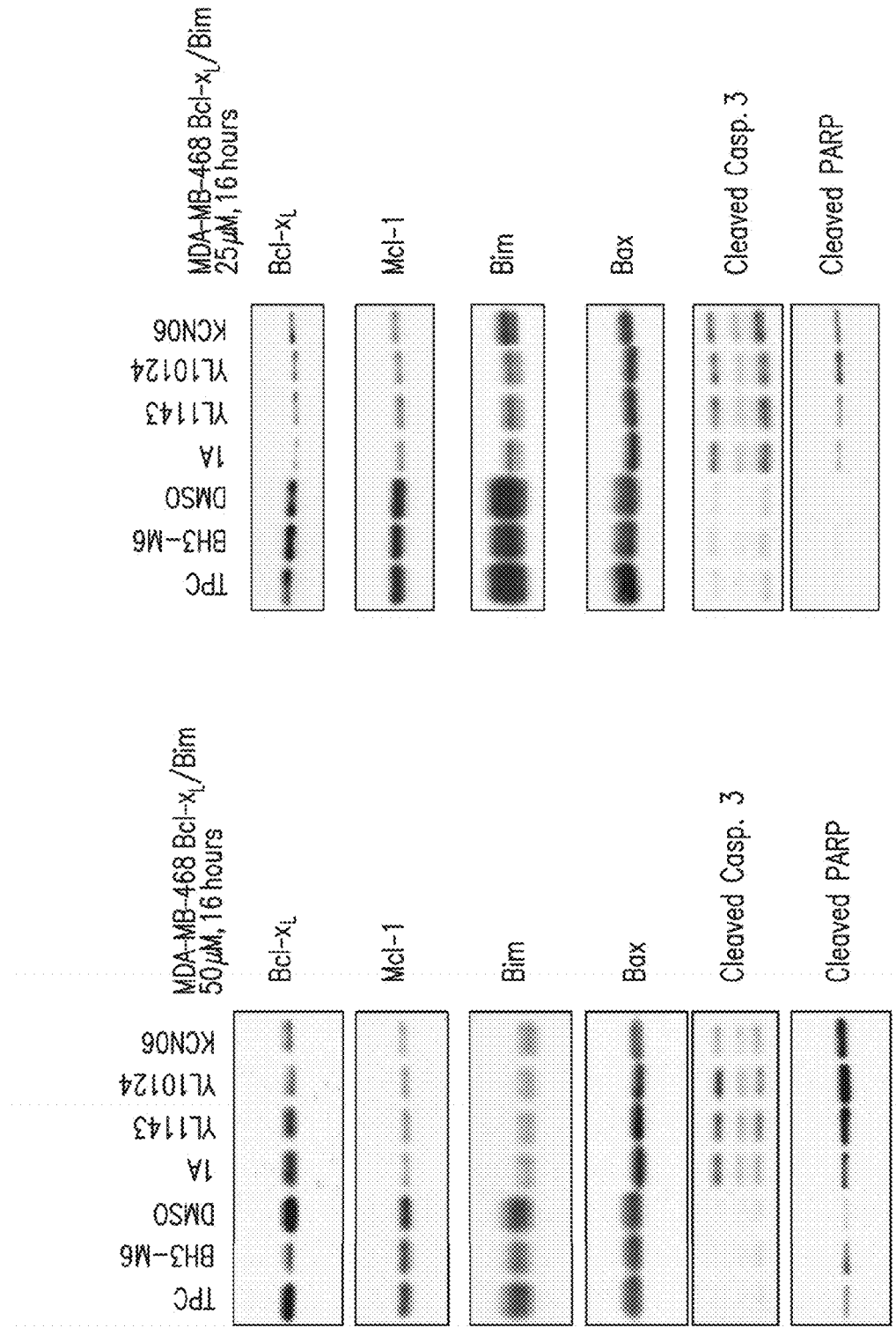
FIG. 2 shows the effects of marinopyrrole derivatives at 50 and 25 μM on pro- and anti-apoptotic proteins after 16 hour treatment of MDA-MB-468 Bcl-xL/Bim cells.

In both figures, "1A" is marinopyrrole A and is used as a control; "YL1143 corresponds to compound 30 as detailed herein, "YL10124" corresponds to compound 8 as detailed herein; and "KCN06" corresponds to compound 38 as detailed herein.

DETAILED DESCRIPTION

The materials, compounds, compositions, articles, and methods described herein may be understood more readily by reference to the following detailed description of specific aspects of the disclosed subject matter and the Examples included therein.

Before the present materials, compounds, compositions, kits, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed, then "less than or equal to" the value, "greater than or equal to the value," and possible ranges between values are also disclosed, as appropriately understood by the skilled artisan. For example, if the value "10" is disclosed, then "less than or equal to 10" as well as "greater than or equal to 10" is also disclosed. It is also understood that throughout the application data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, prevent, inhibit, or eliminate a particular characteristic or event (e.g., tumor growth or survival). The term "control" is used synonymously with the term "treat."

The term "anticancer" refers to the ability to treat or control cellular proliferation and/or tumor growth at any concentration.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

The term "aliphatic" as used herein refers to a non-aromatic hydrocarbon group and includes branched and unbranched, alkyl, alkenyl, or alkynyl groups.

The term "alkyl" as used herein is a branched or unbranched saturated hydrocarbon group of 1 to 24 carbon atoms, such as methyl, ethyl, n-propyl, isopropyl, n-butyl, isobutyl, t-butyl, pentyl, hexyl, heptyl, octyl, nonyl, decyl, dodecyl, tetradecyl, hexadecyl, eicosyl, tetracosyl, and the like. The alkyl group can also be substituted or unsubstituted. The alkyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

The term "alkoxy" as used herein is an alkyl group bound through a single, terminal ether linkage; that is, an "alkoxy" group can be defined as —$OZ^1$ where $Z^1$ is alkyl as defined above.

The term "alkenyl" as used herein is a hydrocarbon group of from 2 to 24 carbon atoms with a structural formula containing at least one carbon-carbon double bond. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C. The alkenyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "alkynyl" as used herein is a hydrocarbon group of 2 to 24 carbon atoms with a structural formula containing at least one carbon-carbon triple bond. The alkynyl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol, as described below.

The term "aryl" as used herein is a group that contains any carbon-based aromatic group including, but not limited to, benzene, naphthalene, phenyl, biphenyl, phenoxybenzene, and the like. The term "heteroaryl" is defined as a group that contains an aromatic group that has at least one heteroatom incorporated within the ring of the aromatic group. Examples of heteroatoms include, but are not limited to, nitrogen, oxygen, sulfur, and phosphorus. The term "non-heteroaryl," which is included in the term "aryl," defines a group that contains an aromatic group that does not contain a heteroatom. The aryl or heteroaryl group can be substituted or unsubstituted. The aryl or heteroaryl group can be substituted with one or more groups including, but not limited to, alkyl, halogenated alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein. The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

The term "cycloalkyl" as used herein is a non-aromatic carbon-based ring composed of at least three carbon atoms. Examples of cycloalkyl groups include, but are not limited to, cyclopropyl, cyclobutyl, cyclopentyl, cyclohexyl, etc. The term "heterocycloalkyl" is a cycloalkyl group as defined above where at least one of the carbon atoms of the ring is substituted with a heteroatom such as, but not limited to, nitrogen, oxygen, sulfur, or phosphorus. The cycloalkyl group and heterocycloalkyl group can be substituted or unsubstituted. The cycloalkyl group and heterocycloalkyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cycloalkenyl" as used herein is a non-aromatic carbon-based ring composed of at least three carbon atoms and containing at least one double bound, i.e., C=C. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," where at least one of the carbon atoms of the ring is substituted with a heteroatom such as, but not limited to, nitrogen, oxygen, sulfur, or phosphorus. The cycloalkenyl group and heterocycloalkenyl group can be substituted or unsubstituted. The cycloalkenyl group and heterocycloalkenyl group can be substituted with one or more groups including, but not limited to, alkyl, alkoxy, alkenyl, alkynyl, aryl, heteroaryl, aldehyde, amino, carboxylic acid, ester, ether, halide, hydroxy, ketone, nitro, silyl, sulfo-oxo, sulfonyl, sulfone, sulfoxide, or thiol as described herein.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

The term "aldehyde" as used herein is represented by the formula —C(O)H. Throughout this specification "C(O)" or "CO" is a short hand notation for C=O.

The terms "amine" or "amino" as used herein are represented by the formula —$NZ^1Z^2$, where $Z^1$ and $Z^2$ can each be substitution group as described herein, such as hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "carboxylic acid" as used herein is represented by the formula —C(O)OH. A "carboxylate" or "carboxyl" group as used herein is represented by the formula —C(O)O⁻.

The term "ester" as used herein is represented by the formula —OC(O)$Z^1$ or —C(O)O$Z^1$, where $Z^1$ can be an alkyl, halogenated alkyl, alkenyl, alkynyl, aryl, heteroaryl, cycloalkyl, cycloalkenyl, heterocycloalkyl, or heterocycloalkenyl group described above.

The term "ether" as used herein is represented by the formula $Z^1OZ^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "ketone" as used herein is represented by the formula $Z^1C(O)Z^2$, where $Z^1$ and $Z^2$ can be, independently, an alkyl, halogenated alkyl, alkenyl, alkynyl, aryl, heteroaryl, cycloalkyl, cycloalkenyl, heterocycloalkyl, or heterocycloalkenyl group described above.

The term "halide" or "halogen" as used herein refers to the fluorine, chlorine, bromine, and iodine.

The term "hydroxyl" as used herein is represented by the formula —OH.

The term "nitro" as used herein is represented by the formula —$NO_2$.

The term "silyl" as used herein is represented by the formula —Si$Z^1Z^2Z^3$, where $Z^1$, $Z^2$, and $Z^3$ can be, independently, hydrogen, alkyl, halogenated alkyl, alkoxy, alkenyl, alkynyl, aryl, heteroaryl, cycloalkyl, cycloalkenyl, heterocycloalkyl, or heterocycloalkenyl group described above.

The term "sulfonyl" is used herein to refer to the sulfo-oxo group represented by the formula —$S(O)_2Z^1$, where $Z^1$ can be hydrogen, an alkyl, halogenated alkyl, alkenyl, alkynyl, aryl, heteroaryl, cycloalkyl, cycloalkenyl, heterocycloalkyl, or heterocycloalkenyl group described above.

The term "sulfonylamino" or "sulfonamide" as used herein is represented by the formula —$S(O)_2NH$—.

The term "thiol" as used herein is represented by the formula —SH.

The term "thio" as used herein is represented by the formula —S—.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

Reference will now be made in detail to specific aspects of the disclosed materials, compounds, compositions, articles, and methods, examples of which are illustrated in the accompanying Examples and Figures.

Compounds

Marinopyrrole derivatives for use as anticancer agents are described herein. The marinopyrrole derivatives can have the following Formula I:

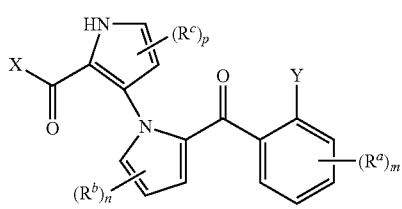

and (+), (−), and (±) isomers, and pharmaceutically acceptable salts and prodrugs thereof.

In Formula I, each $R^a$, $R^b$, and $R^c$ are independently selected from halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl.

Also in Formula I, m is 0, 1, 2, 3, or 4; n is 0, 1, 2, or 3; and p is 0, 1, or 2.

Additionally in Formula I, X and Y are each independently hydrogen, halogen, hydroxyl, substituted or unsubstituted amino, substituted or unsubstituted alkoxyl, substituted or unsubstituted aryloxyl, substituted or unsubstituted alkyl, substituted or unsubstituted heteroalkyl, substituted or unsubstituted aryl, or substituted or unsubstituted heteroaryl.

Further, in this disclosure, excluded from Formula I is marinopyrrole A, i.e., Formula I does not include where $R^b$ and $R^c$ are Cl, m is 0, n and p are both 2, X is aryl with an ortho hydroxy substitution, and Y is hydroxyl. Thus all genera (formulas) and specific variable combinations disclosed herein are subject to this qualification. In some instances, marinopyrrole B (i.e., n is 3 and $R^b$ is Cl, Cl, or Br, p is 2 and $R^c$ is Cl, m is 0, X is aryl with an ortho hydroxy substitution, and Y is hydroxyl).

A class of marinopyrrole derivatives according to Formula I includes compounds represented by Structure A:

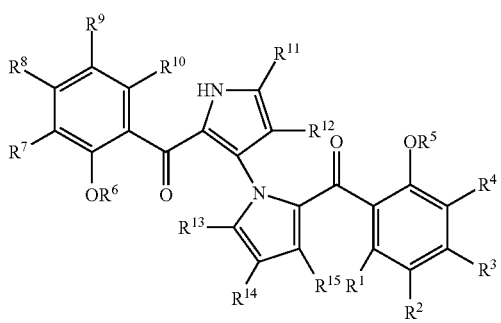

and (+), (−), and (±) isomers, and pharmaceutically acceptable salts and prodrugs thereof.

In Structure A, $R^1$, $R^2$, $R^3$, $R^4$, $R^7$, $R^8$, $R^9$, $R^{10}$, $R^{11}$, $R^{12}$, $R^{13}$, $R^{14}$, and $R^{15}$ are each independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl. In some examples, one of $R^{11}$, $R^{12}$, $R^{13}$, and $R^{14}$ are F, Cl, Br, or I. In other examples, each of $R^{11}$, $R^{12}$, $R^{13}$, and $R^{14}$ are F, Cl, Br, or I.

Again, in this disclosure, excluded from Structure A is marinopyrrole A, i.e., Structure A does not included where $R^1$ through $R^{10}$ and $R^{15}$ are all hydrogen, and $R^{11}$ through $R^{14}$ are all Cl. Thus all genera (formulas) and specific variable combinations disclosed herein are subject to this qualification. Further, in Structure A, the compounds are asymmetric in that the combination of variables for $R^1$ through $R^5$ results in a different moiety than that created by the combination of variables $R^6$ through $R^{10}$. In other words, $R^1$, $R^2$, $R^3$, $R^4$, and $R^5$ are not all the same, respectively, as $R^{10}$, $R^9$, $R^8$, $R^7$, $R^6$. The compounds disclosed herein are also subject to this qualification. In other examples, $R^1$ through $R^4$ and $R^6$ through $R^{10}$ and $R^{15}$ are not hydrogen when each of $R^5$ and $R^6$ are (C(O)CH$_3$), and $R^{11}$ through $R^{14}$ are Cl. In other examples, $R^1$ through $R^{10}$ and $R^{15}$ are not all hydrogen when $R^{11}$ through $R^{14}$ are all Cl. In other examples, $R^1$ through $R^{10}$ are not all hydrogen when $R^{11}$ through $R^{14}$ are all Cl and $R^{15}$ is Br. In other examples, $R^1$ through $R^{10}$ and $R^{15}$ are not all hydrogen when $R^{11}$, $R^{12}$, and $R^{14}$ are all Cl and $R^{13}$ is OCH$_3$. In other examples, $R^1$ through $R^{10}$ and $R^{15}$ are not all hydrogen when $R^{11}$, $R^{12}$, and $R^{14}$ are all Cl and $R^{13}$ is substituted amino.

In Structure A, at least one of $R^2$, $R^3$, and $R^4$ is a halogen. In some examples, $R^1$, $R^2$, $R^3$, $R^4$, $R^7$, $R^8$, $R^9$, and $R^{10}$ are independently selected from hydrogen, OH, O—CH$_3$, O-alkyl, O-heteroalkyl, O-aryl, O-heteroaryl, NH$_2$, NHR$^{16}$ (where $R^{16}$ is alkyl heteroalkyl, aryl, or heteroaryl), NH-alkyl, NH-aryl, NH-heteroaryl, and halogen. In some examples, one or more of $R^1$, $R^2$, $R^3$, $R^4$, $R^7$, $R^8$, $R^9$, and $R^{10}$ are F, Cl, Br, or I. In some examples, one of $R^2$, $R^3$, and $R^4$ is a halogen, such as Cl or F. In some examples, wherein $R^1$ through $R^{10}$ and $R^{15}$ are H, then $R^{13}$ is substituted amino.

Also in Structure A, $R^5$ and $R^6$ are each selected from hydrogen, substituted or unsubstituted alkyl, substituted or unsubstituted heteroalkyl, substituted or unsubstituted aryl, substituted or unsubstituted heteroaryl, and a monovalent cation (e.g., Na$^+$, Li$^+$, K$^+$, or NH4$^+$). In some examples, $R^5$ and $R^6$ are both hydrogen.

Optionally in Structure A, adjacent R groups, e.g., $R^1$ and $R^2$, can be combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl. For example, $R^1$ can be a substituted or unsubstituted ethylene group and $R^2$ can be a substituted or unsubstituted propylene group that combine to form a substituted or unsubstituted phenyl. Other adjacent R groups include the combinations of $R^2$ and $R^3$; $R^3$ and $R^4$; $R^7$ and $R^8$; $R^8$ and $R^9$; $R^9$ and $R^{10}$; $R^{11}$ and $R^{12}$; $R^{13}$ and $R^{14}$; and $R^{14}$ and $R^{15}$.

In some examples of Structure A, $R^1$ and $R^2$ combine to form an unsubstituted phenyl as shown in Structure A-1. In other examples of Structure A, $R^2$ and $R^3$ combine to form an unsubstituted phenyl as shown in Structure A-2. In still other examples of Structure A, $R^3$ and $R^4$ combine to form an unsubstituted phenyl as shown in Structure A-3.

Structure A-1
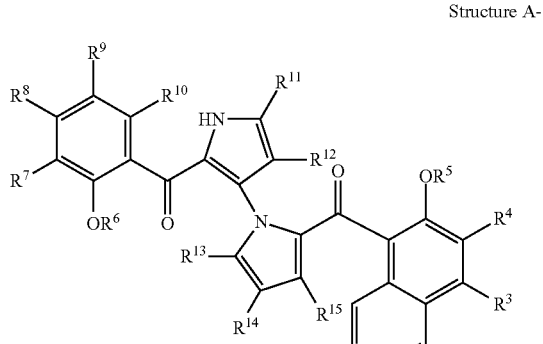

Structure A-2
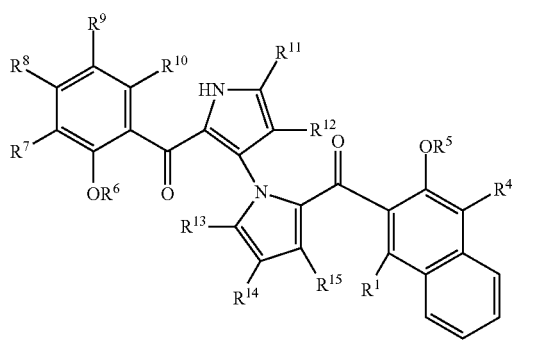

Structure A-3
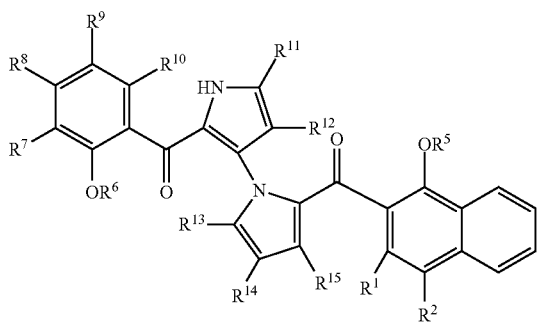

In some examples of Structure A, each of $R^7$, $R^8$, $R^9$, $R^{10}$, and $R^{15}$ are H to form Structure A-4. In other examples of Structure A, each of $R^7$, $R^8$, $R^9$, $R^{10}$, and $R^{15}$ are H and $R^{11}$, $R^{12}$, $R^{13}$, and $R^{14}$ are Cl to form Structure A-5. In still other examples of Structure A, each of $R^7$, $R^8$, $R^9$, $R^{10}$, and $R^{15}$ are H, $R^{11}$, $R^{12}$, and $R^{14}$ are Cl, and $R^{13}$ is substituted amino to form Structure A-6.

Structure A-4
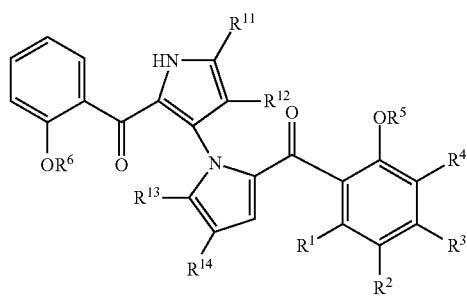

Structure A-5
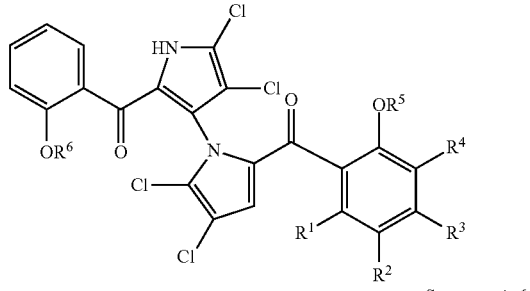

Structure A-6
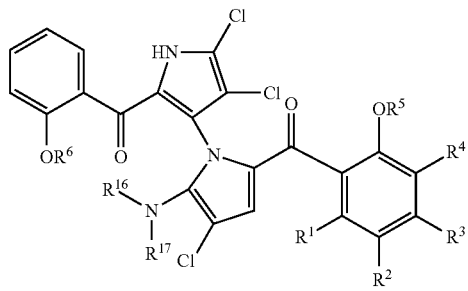

In Structure A-6, $R^{16}$ and $R^{17}$ are each independently selected from hydrogen, substituted or unsubstituted alkyl, substituted or unsubstituted heteroalkyl, substituted or unsubstituted aryl, and substituted or unsubstituted heteroaryl. Optionally, $R^{16}$ and $R^{17}$ can be combined to form a substituted or unsubstituted heteroaryl, substituted or unsubstituted heterocycloalkyl, substituted or unsubstituted heterocycloalkenyl, or substituted or unsubstituted heterocycloalkynyl. In some examples, Structure A-6 does not include $R^1$ through $R^6$ as hydrogen and each of $R^6$ and $R^{17}$ as methyl.

Particular examples of Structure A include the following compounds:

Compound 1
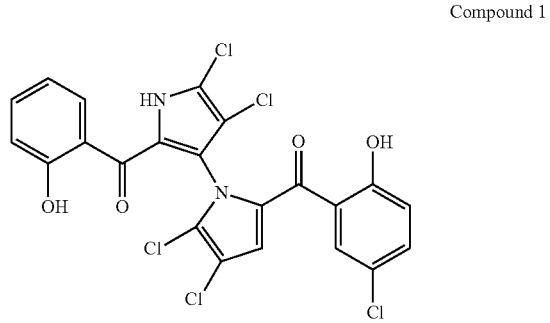

Compound 2
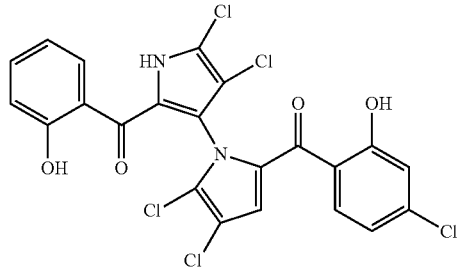

-continued
Compound 3
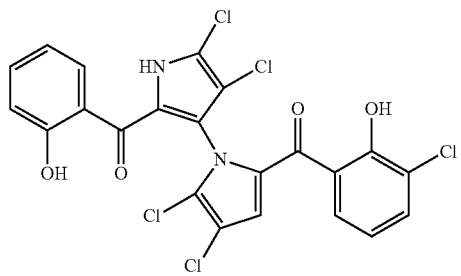
Compound 4
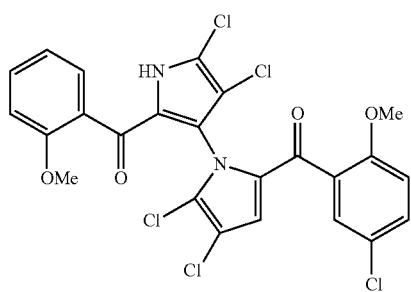
Compound 5
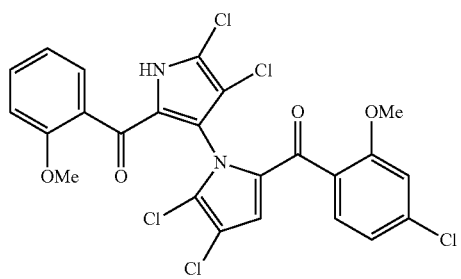
Compound 6
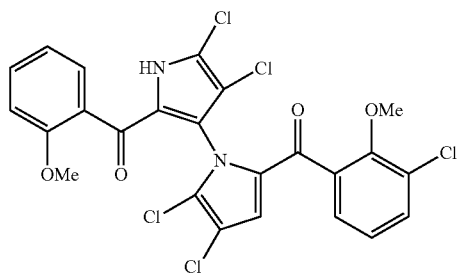
Compound 7
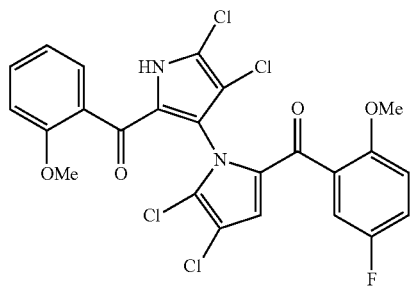
-continued
Compound 8
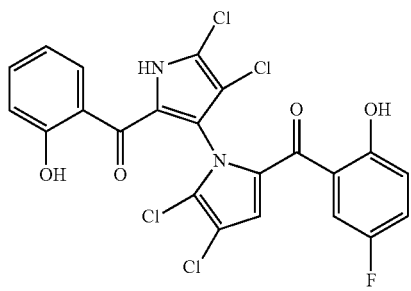
Compound 9
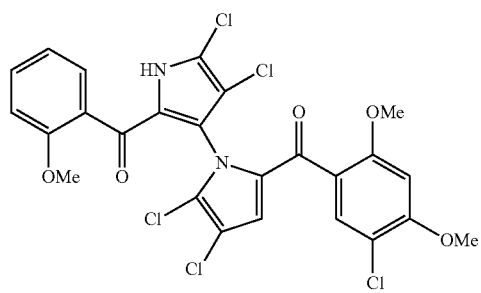
Compound 10
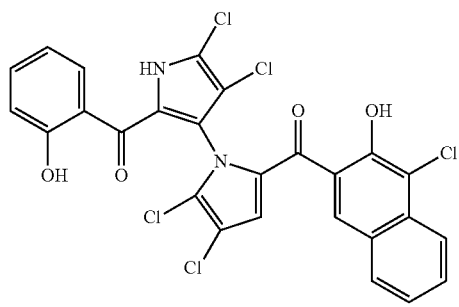
Compound 11
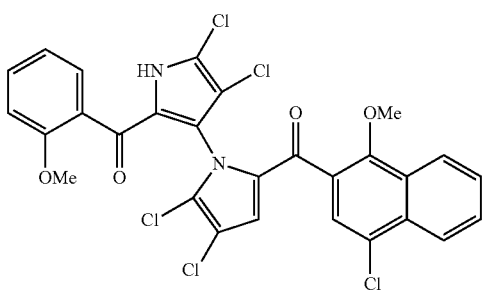
Compound 12
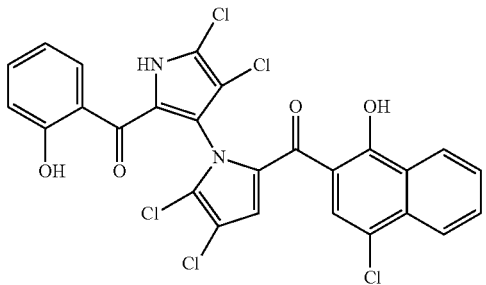

Compound 13
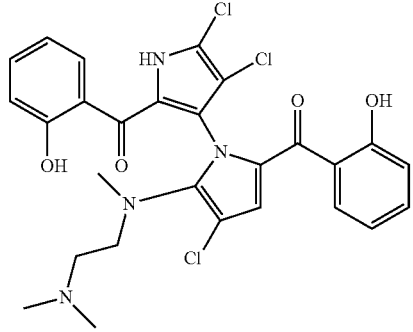
Compound 14
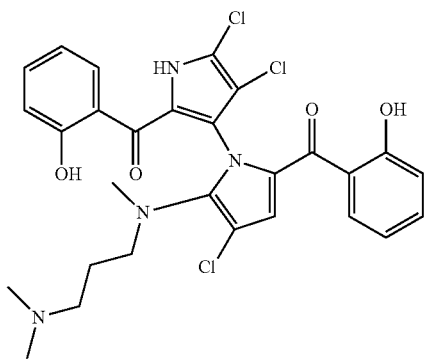
Compound 15
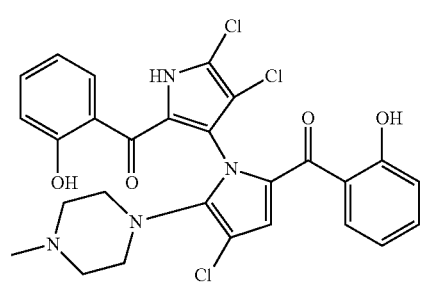
Compound 16
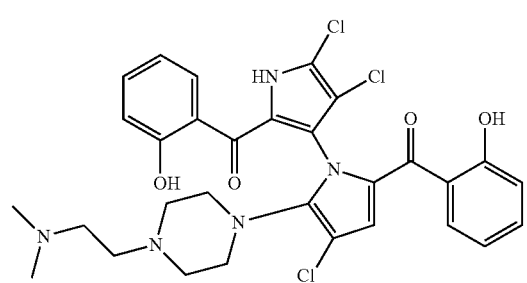
Compound 17
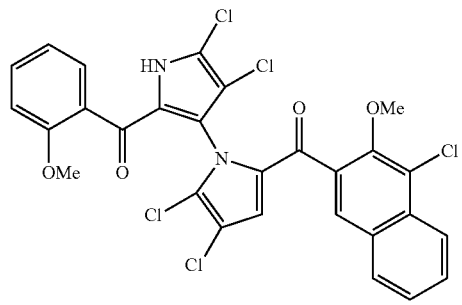
Compound 18
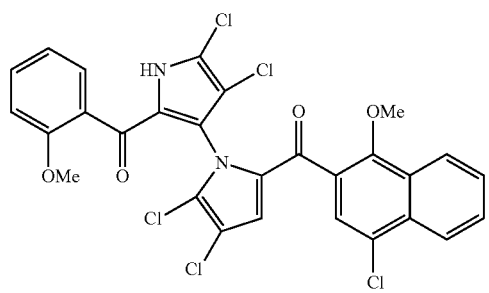
Compound 19
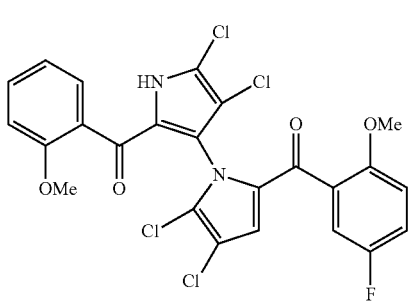
Compound 20
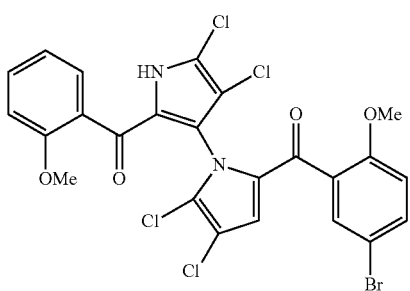
Compound 21
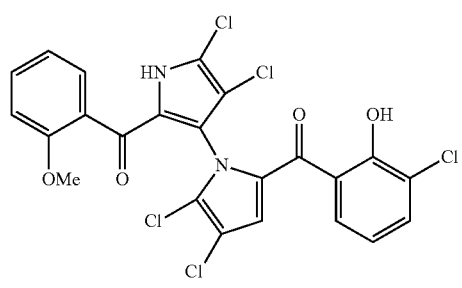

Compound 22
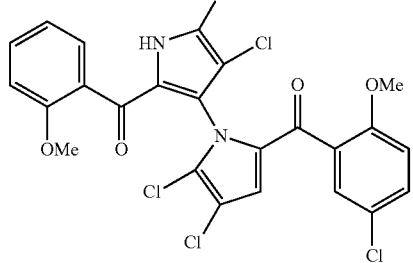
Compound 23
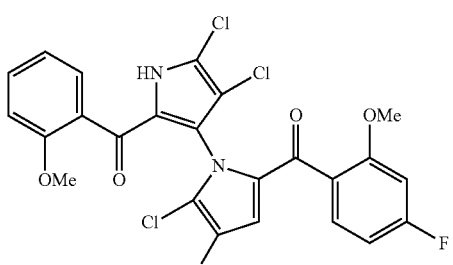
Compound 24
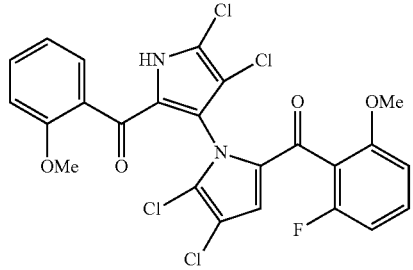
Compound 25
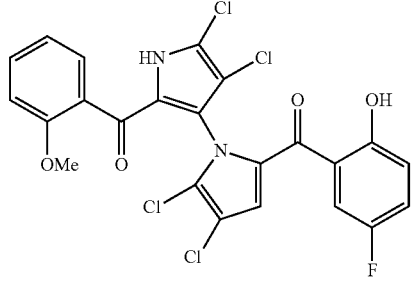
Compound 26
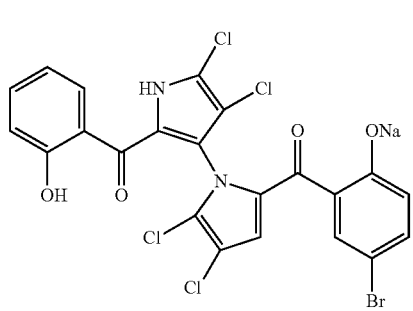
Compound 27
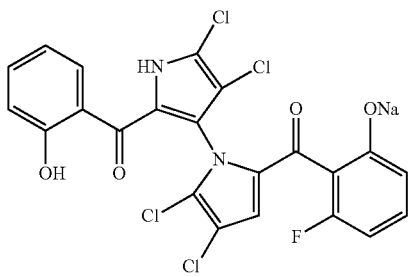
Compound 28
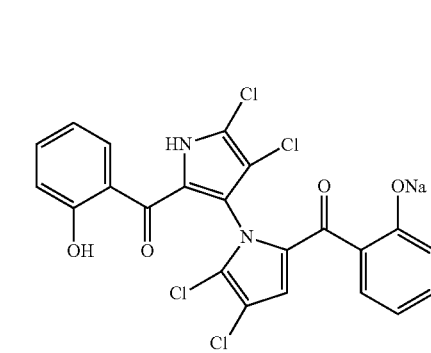
Compound 29
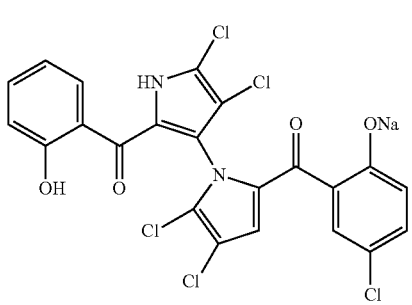
Compound 30
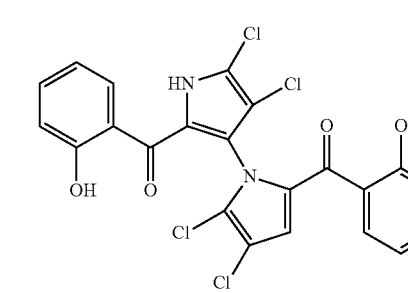
Compound 31
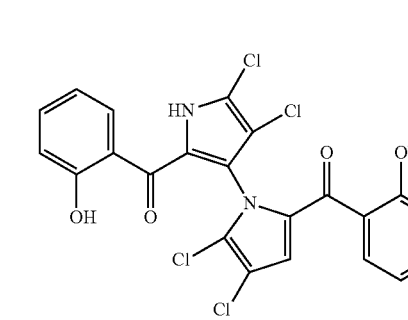

Compound 32

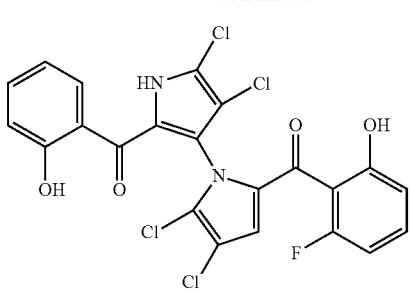

Compound 33

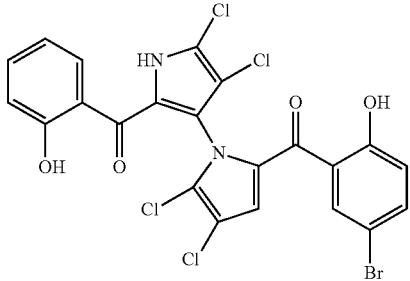

A class of marinopyrrole derivatives according to Formula I includes compounds represented by Structure B:

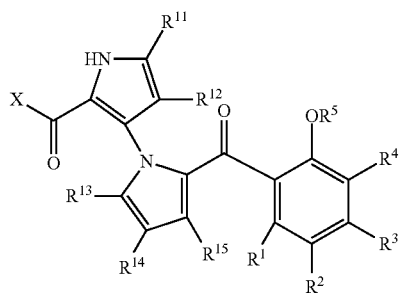

(B)

and (+), (−), and (±) isomers, and pharmaceutically acceptable salts and prodrugs thereof.

In Structure B, $R^1$, $R^2$, $R^3$, $R^4$, $R^{11}$, $R^{12}$, $R^{13}$, $R^{14}$, and $R^{15}$ are each independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl. In some examples, one of $R^{11}$, $R^{12}$, $R^{13}$, and $R^{14}$ are F, Cl, Br, or I. In other examples, each of $R^{11}$, $R^{12}$, $R^{13}$, and $R^{14}$ are F, Cl, Br, or I.

Additionally in Structure B, X is hydroxyl, substituted or unsubstituted alkoxyl, or substituted or unsubstituted amino. In some examples, X is OH.

Also in Structure B, $R^5$ is hydrogen, substituted or unsubstituted alkyl, substituted or unsubstituted heteroalkyl, substituted or unsubstituted aryl, substituted or unsubstituted heteroaryl, or a monovalent cation (e.g., Na$^+$, Li$^+$, K$^+$, or NH4$^+$). In some examples, $R^5$ and $R^6$ are both hydrogen.

In some examples of Structure B, if $R^1$, $R^2$, $R^3$, $R^4$, $R^5$, and $R^{15}$ are H and $R^{11}$, $R^{12}$, $R^{13}$, and $R^{14}$ are Cl, then X is not OEt.

A particular example of Structure B includes the following compound:

Compound 34

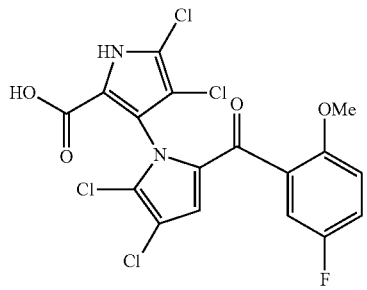

A class of marinopyrrole derivatives according to Formula I includes compounds represented by Structure C:

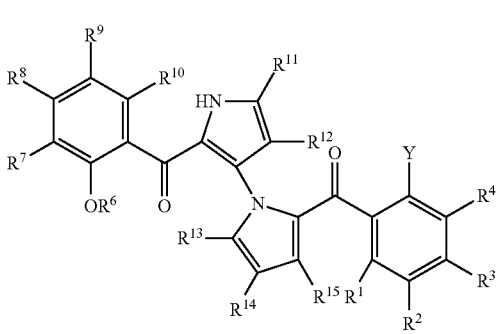

(C)

and (+), (−), and (±) isomers, and pharmaceutically acceptable salts and prodrugs thereof.

In Structure C, $R^1$, $R^2$, $R^3$, $R^4$, $R^7$, $R^8$, $R^9$, $R^{10}$, $R^{11}$, $R^{12}$, $R^{13}$, $R^{14}$, and $R^{15}$ are each independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl. In some examples, one of $R^{11}$, $R^{12}$, $R^{13}$, and $R^{14}$ are F, Cl, Br, or I. In other examples, each of $R^{11}$, $R^{12}$, $R^{13}$, and $R^{14}$ are F, Cl, Br, or I.

Also in Structure C, $R^6$ is selected from hydrogen, substituted or unsubstituted alkyl, substituted or unsubstituted heteroalkyl, substituted or unsubstituted aryl, substituted or unsubstituted heteroaryl, and a monovalent cation (e.g., Na$^+$, Li$^+$, K$^+$, or NH4+). In some examples, $R^5$ and $R^6$ are both hydrogen.

Additionally in Structure C, Y is independently hydrogen, halogen, substituted or unsubstituted alkyl, or substituted or unsubstituted heteroalkyl.

Optionally in Structure C, adjacent groups, e.g., $R^4$ and Y, can be combined to form a substituted or unsubstituted aryl, substituted or unsubstituted heteroaryl, substituted or unsubstituted cycloalkyl, substituted or unsubstituted cycloalkenyl, substituted or unsubstituted cycloalkynyl, substituted or unsubstituted heterocycloalkyl, substituted or unsubstituted heterocycloalkenyl, or substituted or unsubstituted heterocycloalkynyl. For example, $R^1$ can be a substituted or unsubstituted ethylene group and $R^2$ can be a substituted or unsubstituted propylene group that combine to form a substituted or unsubstituted phenyl. Other adjacent R groups include the combinations of $R^1$ and $R^2$; $R^2$ and $R^3$; $R^3$ and $R^4$; $R^7$ and $R^8$; $R^8$ and $R^9$; $R^9$ and $R^{10}$; $R^{11}$ and $R^{12}$; $R^{13}$ and $R^{14}$; and $R^{14}$ and $R^{15}$.

Examples of Structure C include the following compounds:

Compound 35

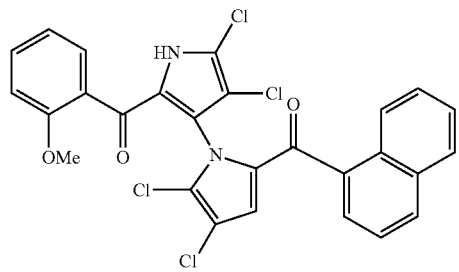

Compound 36

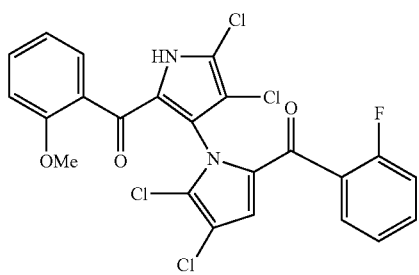

Further marinopyrrole derivatives for use in the methods described herein include the following compounds:

Compound 37

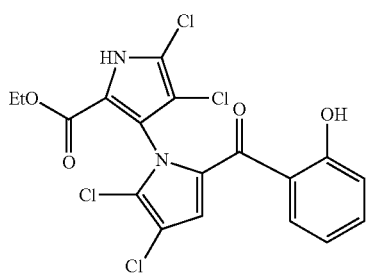

Compound 38

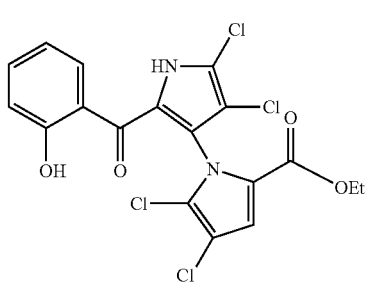

Compound 39

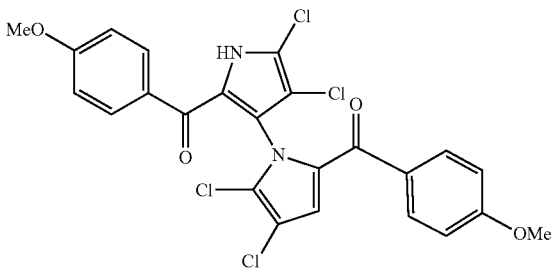

Pharmaceutical Compositions

The compounds described herein or derivatives thereof can be provided in a pharmaceutical composition. Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, can include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences*, 21st Edition, ed. University of the Sciences in Philadelphia, Lippincott, Williams & Wilkins, Philadelphia Pa., 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, N.J.), polyethylene glycol (PEG), and PLURONICS™ (BASF; Florham Park, N.J.). To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total composition including carrier or diluent.

Compositions containing the compound described herein or derivatives thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and *acacia*, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients. The disclosed compounds can also be incorporated into polymers, examples of which include poly(D-L lactide-co-glycolide) polymer for intracranial tumors; poly[bis(pcarboxyphenoxy)propane:sebacic acid] in a 20:80 molar ratio (as used in GLIADEL); chondroitin; chitin; and chitosan.

Liquid dosage forms for oral administration of the compounds described herein or derivatives thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as can be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These can include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught herein.)

Administration of the compounds and compositions described herein or pharmaceutically acceptable salts thereof to a subject can be carried out using therapeutically effective amounts of the compounds and compositions described herein or pharmaceutically acceptable salts thereof as described herein for periods of time effective to treat a disorder.

The effective amount of the compounds and compositions described herein or pharmaceutically acceptable salts thereof as described herein can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about 5 mg/kg of body weight of active compound per day. The expression effective amount, when used to describe an amount of compound in a method, refers to the amount of a compound that achieves the desired pharmacological effect or other effect, for example an amount that results in enzyme inhibition.

Those of skill in the art will understand that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Methods of Making the Compounds

The compounds described herein can be prepared in a variety of ways known to one skilled in the art of organic synthesis or variations thereon as appreciated by those skilled in the art. The compounds described herein can be prepared from readily available starting materials. Optimum reaction conditions can vary with the particular reactants or solvents used, but such conditions can be determined by one skilled in the art.

Variations on Formula I include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1H$ or $^{13}C$) infrared spectroscopy, spectrophotometry (e.g., UV-visible), or mass spectrometry, or by chromatography such as high performance liquid chromatography (HPLC) or thin layer chromatography.

Compounds of Formula I can be prepared using the exemplary synthesis outlined in Scheme 1. Briefly, 2-ethoxycarbonyl-3-aminopyrrole (a) was obtained using a published procedure (Furneaux et al., *J. Org. Chem.* (1999), 64, 8411-8412). A PPTS-promoted Clauson-Kaas reaction (Nicolaou et al., *Tet. Lett.* (2011), 52, 2041-2043; Rochais et al., *Bioorg. Med. Chem.* (2006), 14, 8162-8175) between (a) and 2,5-dimethoxytetrahydrafuran (b) in dioxane under reflux gave rise to bispyrrole (c) in 53% yields. The mono-addition of lithiated anisole (d) to bispyrrole ester (c) in THF at −78° C. furnished mono acylated bispyrrole (e) in 85% yield (Nicolaou et al., *Tet. Lett.* (2011), 52, 2041-2043). Friedel-Crafts arylation of (e) with the acid chlorides (g), generated in situ from the corresponding carboxylic acids (f) with thionyl chloride, afforded a series of marinopyrrole precursor (h-j). A novel series of asymmetrical marinopyrrole derivatives, Compounds 5, 4, and 6, were obtained by tetrachlorination of the corresponding (h), (i), and (j), respectively, using 4.1 equivalents of sulfuryl chloride ($SO_2Cl_2$) in DCM at 0° C. Demethylation of Compounds 5, 4, and 6 using $BBr_3$ in DCM furnished Compounds 2, 1, and 3, respectively, in >90% yield (Scheme 1) (Nicolaou et al., *Tet. Lett.* (2011), 52, 2041-2043; Cheng et al., *J. Comb. Chem.* (2010), 12, 541-547).

Scheme 1:

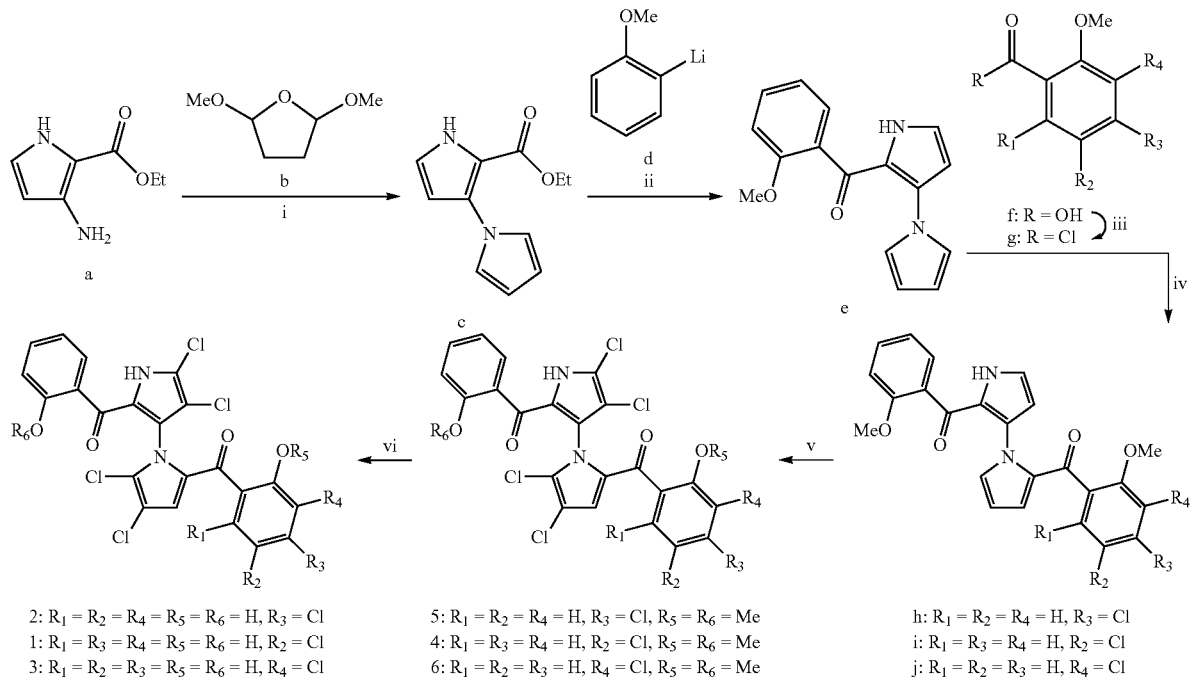

2: $R_1 = R_2 = R_4 = R_5 = R_6 = H, R_3 = Cl$
1: $R_1 = R_3 = R_4 = R_5 = R_6 = H, R_2 = Cl$
3: $R_1 = R_2 = R_3 = R_5 = R_6 = H, R_4 = Cl$

5: $R_1 = R_2 = R_4 = H, R_3 = Cl, R_5 = R_6 = Me$
4: $R_1 = R_3 = R_4 = H, R_2 = Cl, R_5 = R_6 = Me$
6: $R_1 = R_2 = R_3 = H, R_4 = Cl, R_5 = R_6 = Me$ h: $R_1 = R_2 = R_4 = H, R_3 = Cl$
i: $R_1 = R_3 = R_4 = H, R_2 = Cl$
j: $R_1 = R_2 = R_3 = H, R_4 = Cl$

<sup>a</sup>Conditions: (i) PPTS, 1,4-dioxane, reflux, 53%. (ii) 6.0 eq. d, THF, -78° C., 85%. (iii) SOCl$_2$, benzene, reflux. (iv) 1.2 eq. g, 1.3 eq. AlCl$_3$, DCM, 0-25° C., 70%. (v) 1.0 eq. h, 4.1 eq. SO$_2$Cl$_2$, DCM, 0° C., 85%. (vi) 1.0 eq. 5, 4.0 eq. BBr$_3$, DCM, -78° C., 96%.

Activity Assays

The activity of the compounds provided herein as anticancer agents can be measured in standard assays, e.g., HPLC assays. The activities of the compounds as determined using the assays described herein can be reported in terms of IC$_{50}$. As used herein, IC$_{50}$ refers to an amount, concentration, or dosage of a particular test compound that achieves a 50% inhibition of a maximal response in an assay that measures such response.

In certain aspects, the disclosed compounds and compositions need not actually be synthesized, but instead can be used as targets for any molecular modeling technique to predict and characterize interactions with cancer associated enzymes. This is achieved through structural information and computer modeling. Computer modeling technology allows visualization of the three-dimensional atomic structure of a selected molecule and the rational design of new compounds that will interact with an enzyme. The three-dimensional construct of the enzyme typically depends on data from x-ray crystallographic analyses or NMR imaging of the selected molecule. The molecular dynamics require force field data (e.g., Merck Molecular Force Field). The computer graphics systems enable prediction of how a new compound will link to the enzyme and allow experimental manipulation of the structures of the compound to perfect binding specificity. Prediction of what the interactions will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other. Upon identification of compounds that interact in a desired way with the enzyme in silico, actual compounds can be synthesized and assayed as disclosed herein.

Methods of Use

Provided herein are methods of treating, preventing, or ameliorating cancer in a subject. The methods include administering to a subject an effective amount of one or more of the compounds or compositions described herein, or a pharmaceutically acceptable salt thereof. The compounds and compositions described herein or pharmaceutically acceptable salts thereof are useful for treating cancer in humans, e.g., pediatric and geriatric populations, and in animals, e.g., veterinary applications. The disclosed methods can optionally include identifying a patient who is or can be in need of treatment of a cancer. Examples of cancer types treatable by the compounds and compositions described herein include bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples inclued cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells). Specific cancers contemplated for treatment include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma. Treatment of breast cancer by administering the disclosed compounds is particularly preferred.

The methods of treatment or prevention described herein can further include treatment with one or more additional agents (e.g., an anti-cancer agent or ionizing radiation). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents.

For example, the compounds or compositions or pharmaceutically acceptable salts thereof as described herein can be combined into a pharmaceutical composition with an additional anti-cancer agent, such as 13-cis-Retinoic Acid, 2-Amino-6-Mercaptopurine, 2-CdA, 2-Chlorodeoxyadenosine, 5-fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-transretinoic acid, Alpha interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, *Erwinia* L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, -Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (interferon alfa-2b), Leucovorin, Leukeran, Leukine, Leuprolide, Leucrocistine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-asparaginase, and LCR. The additional anti-cancer agent can also include biopharmaceuticals such as, for example, antibodies.

Further, the additional agent can include ABT-263 (CAS#923564-51-6) also known as navitoclax and/or ABT-737 (CAS#852808-04-9), both of which are commercially. Still further the disclosed compositions can further include compounds that inhibit transcription of Mcl-1, such as with the cyclin-dependent kinase inhibitors Seliciclib (CAS#186692-46-6) and Flavopiridol (CAS#146426-40-6) or translation, such as with the multikinase inhibitor BAY 43-9006 (CAS#284461-73-0). Further examples of additional compounds that can be present in the disclosed compositions include, but are not limited to, dexamethasone (CAS#50-02-2), melphalan (CAS#148-82-3), obatoclax (CAS#803712-67-6), BH3-M6, and gossypol (CAS#303-45-7).

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease. For example, the compounds can be used with mutant herpes simplex virus in the treatment of non-small cell lung cancer (Toyoizumi, et al., "Combined therapy with chemotherapeutic agents and herpes simplex virus type IICP34.5 mutant (HSV-1716) in human non-small cell lung cancer," *Human Gene Therapy*, 1999, 10(18): 17).

Also described herein are methods of killing a tumor cell in a subject. The method includes contacting the tumor cell with an effective amount of a compound or composition as described herein, and optionally includes the step of irradiating the tumor cell with an effective amount of ionizing radiation. Additionally, methods of radiotherapy of tumors are provided herein. The methods include contacting the tumor cell with an effective amount of a compound or composition as described herein, and irradiating the tumor with an effective amount of ionizing radiation. As used herein, the term ionizing radiation refers to radiation comprising particles or photons that have sufficient energy or can produce sufficient energy via nuclear interactions to produce ionization. An example of ionizing radiation is x-radiation. An effective amount of ionizing radiation refers to a dose of ionizing radiation that produces an increase in cell damage or death when administered in combination with the compounds described herein. The ionizing radiation can be delivered according to methods as known in the art, including administering radiolabeled antibodies and radioisotopes.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection. Prophylactic administration can be used, for example, in the chemopreventative treatment of subjects presenting precancerous lesions, those diagnosed with early stage malignancies, and for subgroups with susceptibilities (e.g., family, racial, and/or occupational) to particular cancers. Therapeutic treatment involves administering to a subject a therapeutically effective amount of the compounds and compositions or pharmaceutically acceptable salts thereof as described herein after cancer is diagnosed.

Because the compounds disclosed herein are effective at inhibiting Mcl-1, they can be particularly effective for treating cancers where Mcl-1 is expressed or over expressed, and killing Mcl-1 dependent cells.

Kits

Also provided herein are kits for treating or preventing cancer in a subject. A kit can include any of the compounds or compositions described herein. For example, a kit can include a compound of Formula I. A kit can further include one or more anti-cancer agents (e.g., paclitaxel). A kit can include an oral formulation of any of the compounds or compositions described herein. A kit can additionally include directions for use of the kit (e.g., instructions for treating a subject).

To provide for the administration of such dosages for the desired therapeutic treatment, in some embodiments, pharmaceutical compositions disclosed herein can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The examples below are intended to further illustrate certain aspects of the methods and compounds described herein, and are not intended to limit the scope of the claims.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

Synthesis of Compounds

All chemicals and solvents were purchased from commercial suppliers and used without further purification. Preparative flash column chromatography was performed on silica gel 60, 0.040-0.063 mm (EMD Chemicals; Gibbstown, N.J.). $^{1}$H NMR (400 MHz) spectra were recorded on a Varian AS400 with a 60-place automated sample changer. High resolution ESI-MS spectra were recorded on an Agilent ESI-TOF LC-MS 6200 system. Preparative HPLC was performed on a Gilson HPLC system with UV detectors and Gilson 215 liquid handler for auto injection and fraction collections (customized by HT Labs; San Diego, Calif.). Analytical HPLC was performed on an Agilent 1100 series with diode array detectors and auto samplers. The specifications of HPLC analysis are as follows: flow rate, 1 mL/min; column, Intertsil, 2.5 μm, 4.6×150 mm; wavelength, 254 and 280 nm; mobile phase, A: H$_2$O with 0.1% HCO$_2$H, B: MeOH, gradient of 50-95% B in 25 min. All tested compounds possessed a purity of not less than 95%.

Ethyl 1'H-1,3'-bipyrrole-2'-carboxylate (c)

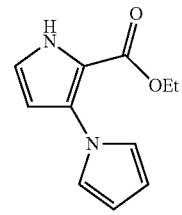 [SMILES: CCOC(=O)c1[nH]ccc1-n1cccc1]

To a stirred solution of 2,5-dimethoxytetrahydrofuran (b) (1.6 mL, 12.4 mmol, 1.3 equiv) and PPTS (3.2 g, 12.4 mmol, 1.3 equiv) in 1,4-dioxane (20 mL) at 50° C., a solution of aminopyrrole (a) (1.47 g, 9.55 mmol, 1.0 eq.) in 1,4-dioxane (6 mL) was added slowly. The resulting mixture was brought to reflux and stirred for 1 h. The reaction mixture was then concentrated, dissolved in EtOAc (50 mL) and dried over anhydrous MgSO$_4$. The crude product was purified by flash column chromatography (10% EtOAc in Hexane) to give (c) as a yellow solid (1.036 g, 53% yield). $^1$H NMR (400 MHz, CDCl$_3$) δ 8.99 (s, 1H), 7.04-7.01 (m, 2H), 6.89 (t, J=3.1 Hz, 1H), 6.29 (t, J=2.9 Hz, 1H), 6.27-6.24 (m, 2H), 4.28 (q, J=7.1 Hz, 2H), 1.29 (t, J=7.1 Hz, 3H).

1'H-1,3'-Bipyrrol-2'-yl(2-methoxyphenyl)methanone (e)

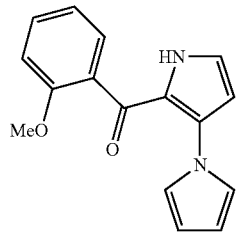 [SMILES: COc1ccccc1C(=O)c1[nH]ccc1-n1cccc1]

To a solution of 2-bromoanisole (1.39 g, 7.43 mmol, 5.63 equiv) in anhydrous THF (5 mL) at −78° C., a 2.5M solution of BuLi in hexane (3 mL, 7.50 mmol, 5.68 eq.) was added dropwise, the resulting mixture was stirred for 1 h. at −78° C. to generate the lithiated anisole. In an oven-dried flask, compound (c) (270 mg, 1.32 mmol, 1 eq.) was dissolved in THF (5 mL) and cooled to −78° C., the lithiated anisole (d) was transferred into the solution containing (c) dropwise via syringe, and the resulting mixture was stirred for 1 h. at −78° C. To the reaction mixture, an aqueous solution of NH$_4$Cl (5 mL) was added, the mixture was extracted with EtOAc, dried over anhydrous Na$_2$SO$_4$. The crude product was purified by flash column chromatography (10% EtOAc in Hexane) to give (e) as a light brown solid (0.30 g, 85% yield).

$^1$H NMR (400 MHz, CDCl$_3$) δ 9.35 (s, 1H), 7.28-7.22 (m, 1H), 7.20 (dd, J=7.5, 1.7 Hz, 1H), 7.02 (t, J=3.0 Hz, 1H), 6.80 (td, J=7.5, 0.9 Hz, 1H), 6.68 (d, J=8.4 Hz, 1H), 6.48-6.43 (m, 2H), 6.27 (t, J=2.8 Hz, 1H), 5.88 (m, 2H), 3.63 (s, 3H).

(2-(4-Chloro-2-methoxybenzoyl)-1'H-1,3'-bipyrrol-2'-yl)(2-methoxyphenyl)methanone (h)

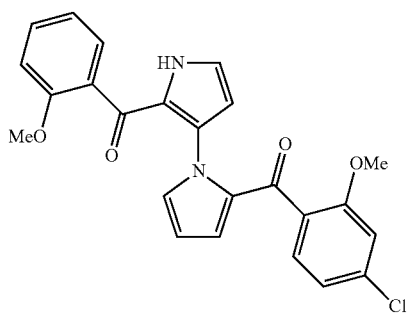 [SMILES: COc1ccccc1C(=O)c1[nH]ccc1-n1cccc1C(=O)c1ccc(Cl)cc1OC]

Into a solution of 4-chloro-2-methoxybenzoic acid (125 mg, 0.67 mmol, 1.2 eq.) in benzene (1.5 mL), SOCl$_2$ (1.5 mL) was added at room temperature and the resulting solution was refluxed for 2 h. The reaction mixture was concentrated under vacuum to generate 4-chloro-2-methoxybenzoyl chloride which was used directly in the next step without purification. A solution of 4-chloro-2-methoxybenzoyl chloride in DCM (2 mL) was added to a slurry of AlCl$_3$ (96 mg, 1.3 eq.) in DCM (2.5 mL) at 0° C. and then a solution of (e) (150 mg, 0.56 mmol, 1.0 equiv) in DCM (1.5 mL) was added dropwise. The resulting solution was allowed to warm to room temperature and stirred overnight. A saturated solution of NaHCO$_3$ (10 mL) and DCM (10 mL) was then added and the resulting mixture was stirred for 1 h, and then filtered though Celite®. The mixture was extracted with DCM (2×10 mL), the organic layer was dried over anhydrous Na$_2$SO$_4$, and purified by flash column chromatography (hexanes:EtOAc) to afford 172 mg of (h) as a white solid, 70% yield. $^1$H NMR (400 MHz, CDCl$_3$) δ 9.83 (s, 1H), 7.22-7.14 (m, 2H), 7.12 (d, J=7.8 Hz, 1H), 7.04 (t, J=3.0 Hz, 1H), 6.95-6.88 (m, 2H), 6.73-6.63 (m, 3H), 6.31 (dd, J=4.0, 1.7 Hz, 1H), 6.27 (t, J=2.8 Hz, 1H), 5.83 (dd, J=4.0, 2.6 Hz, 1H), 3.77 (s, 3H), 3.69 (s, 3H).

(2-(5-Chloro-2-methoxybenzoyl)-1'H-1,3'-bipyrrol-2'-yl)(2-methoxyphenyl)methanone (i)

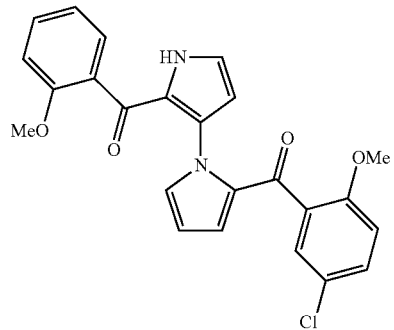 [SMILES: COc1ccccc1C(=O)c1[nH]ccc1-n1cccc1C(=O)c1cc(Cl)ccc1OC]

5-Chloro-2-methoxybenzoyl chloride was generated in situ from the corresponding acid using the same method as described above for 4-chloro-2-methoxybenzoyl chloride. Compound (i) (88 mg, 67% yield) was obtained using the same method as (h) described above. $^1$H NMR (400 MHz, CDCL3) δ 9.78 (s, 1H), 7.31 (dd, J=8.8, 2.7 Hz, 1H), 7.25-7.15 (m, 2H), 7.06 (dd, J=4.3, 1.7 Hz, 2H), 6.85 (d, J=8.9 Hz, 1H), 6.77-6.66 (m, 3H), 6.32 (dd, J=4.0, 1.7 Hz, 1H), 6.30 (t, J=2.8 Hz, 1H), 5.87 (dd, J=4.0, 2.6 Hz, 1H), 3.75 (s, 3H), 3.69 (s, 3H).

(2-(3-Chloro-2-methoxybenzoyl)-1'H-1,3'-bipyrrol-2'-y)(2-methoxyphenyl)methanone (j)

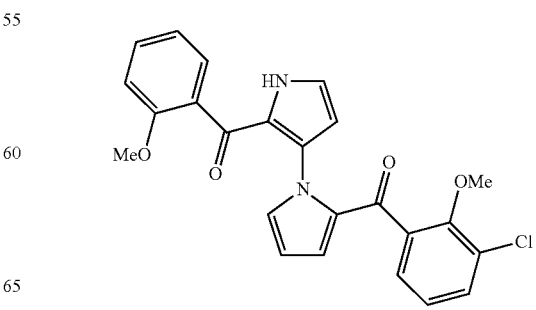

3-Chloro-2-methoxybenzoyl chloride was generated in situ from the corresponding acid using the same method as described above for 4-chloro-2-methoxybenzoyl chloride. Compound (j) (90 mg, 68% yield) was obtained using the same method as (h) described above. $^1$H NMR (400 MHz, CDCL$_3$) δ 9.81 (s, 1H), 7.52 (dd, J=7.8, 1.6 Hz, 1H), 7.39 (dd, J=8.0, 1.6 Hz, 1H), 7.24-7.19 (m, 1H), 7.10 (dt, J=5.7, 2.2 Hz, 2H), 6.87 (dd, J=2.6, 1.6 Hz, 1H), 6.79 (d, J=7.9 Hz, 1H), 6.66-6.59 (m, 3H), 6.31 (t, J=2.8 Hz, 1H), 6.05 (dd, J=4.1, 2.6 Hz, 1H), 3.57 (s, 3H), 3.52 (s, 3H).

(4-Chloro-2-methoxyphenyl)(4,4',5,5'-tetrachloro-2'-(2-methoxybenzoyl)-1'H-[1,3'-bipyrrole]-2-yl)methanone (Compound 5)

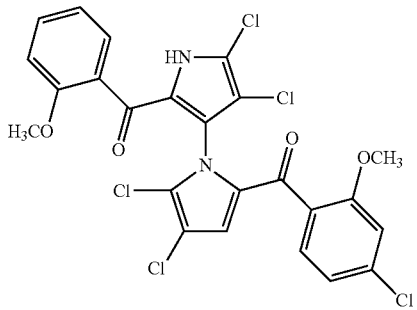 [SMILES: COc1ccccc1C(=O)c1[nH]c(Cl)c(Cl)c1-n1c(C(=O)c2ccc(Cl)cc2OC)cc(Cl)c1Cl]

To a solution of compound (h) (82 mg, 0.19 mmol, 1 eq.) in DCM (5 mL) at 0° C., SO$_2$Cl$_2$ (64 μL, 0.78 mmol, 4.1 equiv) was added dropwise, and the solution was allowed to stir at 0° C. for 1 h. Saturated aqueous NaHCO$_3$ solution (2 mL) was added and the resulting mixture was extracted with DCM (3×4 mL). The combined organic layers were dried with anhydrous MgSO$_4$, filtered, and concentrated. The residue was purified by flash column chromatography (silica gel, hexanes:EtOAc 4:1) to afford Compound 5 (92 mg, 85% yield) as an off-white solid.
$^1$H NMR (400 MHz, CDCl$_3$) δ 10.38 (s, 1H), 7.25-7.21 (m, 2H), 7.13 (d, J=7.9 Hz, 1H), 6.96-6.94 (m, 2H), 6.76 (d, J=8.3 Hz, 1H), 6.68 (t, J=7.8 Hz, 1H), 6.31 (s, 1H), 3.80 (s, 3H), 3.72 (s, 3H); HRMS (ESI-TOF) [M+H]$^+$ calcd for C$_{24}$H$_{16}$Cl$_5$N$_2$O$_4$ 570.9547. found 570.9537; HPLC purity, 95.2%.

(5-Chloro-2-methoxyphenyl)(4,4',5,5'-tetrachloro-2'-(2-methoxybenzoyl)-1'H-1,3'-bipyrrol-2-yl)methanone (Compound 4)

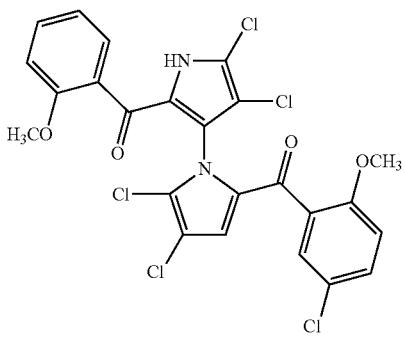 [SMILES: COc1ccccc1C(=O)c1[nH]c(Cl)c(Cl)c1-n1c(C(=O)c2cc(Cl)ccc2OC)cc(Cl)c1Cl]

The same procedure described for Compound 5 was used to synthesize Compound 4 (87 mg, 80% yield). $^1$H NMR (400 MHz, CDCl$_3$) δ 10.28 (s, 1H), 7.36 (dd, J=8.9, 2.7 Hz, 1H), 7.31-7.27 (m, 1H), 7.19 (dd, J=7.5, 1.7 Hz, 1H), 7.07 (d, J=2.6 Hz, 1H), 6.88 (d, J=8.9 Hz, 1H), 6.79 (d, J=8.4 Hz, 1H), 6.73 (td, J=7.5, 0.8 Hz, 1H), 6.33 (s, 1H), 3.78 (s, 3H), 3.73 (s, 3H).

(3-Chloro-2-methoxyphenyl)(4,4',5,5'-tetrachloro-2'-(2-methoxybenzoyl)-1H-1,3'-bipyrrol-2-yl)methanone (Compound 6)

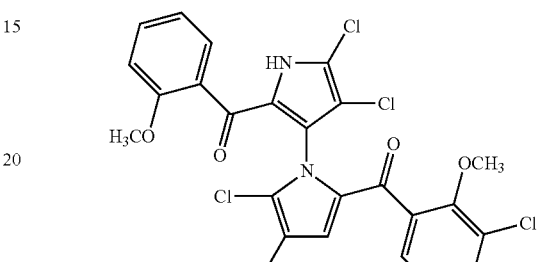

The same procedure described for Compound 5 was used to synthesize Compound 6 (80 mg, 74%). $^1$H NMR (400 MHz, CDCl$_3$) δ 10.30 (s, 1H), 7.57 (dd, J=7.9, 1.5 Hz, 1H), 7.37-7.27 (m, 2H), 7.11 (dd, J=7.5, 1.7 Hz, 1H), 6.85 (t, J=7.9 Hz, 1H), 6.76 (d, J=8.4 Hz, 1H), 6.67 (t, J=7.5 Hz, 1H), 6.57 (s, 1H), 3.83 (s, 3H), 3.73 (s, 3H).

(4-Chloro-2-hydroxyphenyl)(4,4',5,5'-tetrachloro-2'-(2-hydroxybenzoyl)-1'H-1,3'-bipyrrol-2-yl)methanone (Compound 2)

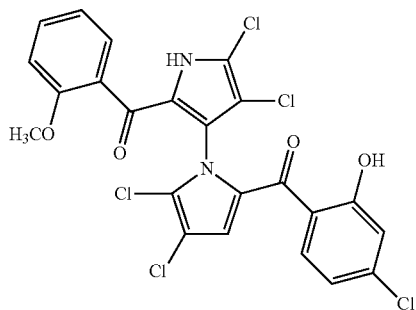 [SMILES: COc1ccccc1C(=O)c1[nH]c(Cl)c(Cl)c1-n1c(C(=O)c2ccc(Cl)cc2O)cc(Cl)c1Cl]

To a solution of Compound 5 (33 mg, 0.058 mmol) in anhydrous DCM (1 mL) was slowly added 1.0 M solution of BBr$_3$ in DCM (23 μL, 0.23 mmol, 4 eq.) via a syringe under N$_2$ at −78° C. After being stirred for 0.5 h, the mixture was quenched by addition of MeOH (0.5 mL) and extracted with DCM (3×10 mL). The combined organic layers were dried over anhydrous MgSO$_4$, filtered and concentrated in vacuum. The residue was purified by column chromatography (silica gel, hexanes: 12% EtOAc) to give Compound 2 (30 mg, 96% yield) as a yellow solid. $^1$H NMR (400 MHz, CDCl$_3$) δ 11.34 (s, 1H), 10.39 (s, 1H), 9.77 (s, 1H), 7.47 (d, J=8.6 Hz, 1H), 7.43 (dd, J=8.0, 1.7 Hz, 1H), 7.36 (ddd, J=8.8, 7.4, 1.6 Hz, 1H), 7.04 (d, J=2.0 Hz, 1H), 6.95-6.90 (m, 1H), 6.87 (dd, J=8.6, 2.0 Hz, 1H), 6.68 (s, 1H), 6.53 (ddd, J=8.0, 7.3, 1.1 Hz, 1H); HRMS (ESI-TOF) [M+H]⁺ calcd for $C_{22}H_{12}Cl_5N_2O_4$ 542.9234. found 542.9237; HPLC purity 96.6%.

(5-Chloro-2-hydroxyphenyl)(4,4',5,5'-tetrachloro-2'-(2-hydroxybenzoyl)-1'H-1,3'-bipyrrol-2-yl)methanone (Compound 1)

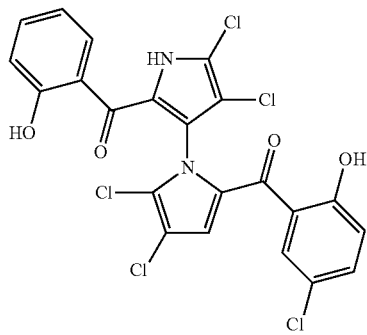 [SMILES: O=C(c1ccccc1O)c1[nH]c(Cl)c(Cl)c1-n1c(C(=O)c2cc(Cl)ccc2O)cc(Cl)c1Cl]

The same procedure as Compound 2 was followed to obtain Compound 1 (28 mg, 90%) from Compound 4 (31 mg, 0.055 mmol). $^1$H NMR (400 MHz, CDCl$_3$) δ 11.10 (s, 1H), 10.33 (s, 1H), 9.89 (s, 1H), 8.06 (dd, J=7.9, 1.8 Hz, 1H), 7.95 (d, J=2.4 Hz, 1H), 7.83 (d, J=8.3 Hz, 1H), 7.71-7.64 (m, 1H), 7.49-7.41 (m, 2H), 6.97 (dd, J=8.9, 2.1 Hz, 1H), 6.87 (s, 1H); HRMS (ESI-TOF) [M+Na]⁺ calcd for $C_{22}H_{11}Cl_5N_2O_4Na$ 564.9054. found 564.9055; HPLC purity, 95.0%.

(3-Chloro-2-hydroxyphenyl)(4,4',5,5'-tetrachloro-2'-(2-hydroxybenzoyl)-1'H-1,3'-bipyrrol-2-yl)methanone (Compound 3)

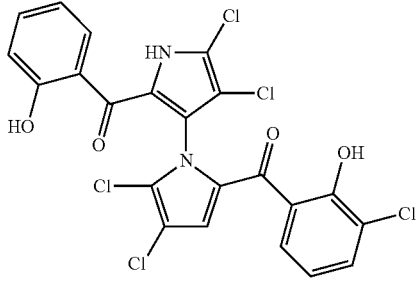 [SMILES: O=C(c1ccccc1O)c1[nH]c(Cl)c(Cl)c1-n1c(C(=O)c2cccc(Cl)c2O)cc(Cl)c1Cl]

The same procedure as Compound 2 was followed to obtain Compound 3 (26 mg, 91%) from Compound 6 (29 mg, 0.05 mmol). $^1$H NMR (400 MHz, CDCl$_3$) δ 11.74 (s, 1H), 10.48 (s, 1H), 9.93 (s, 1H), 8.06 (d, J=7.9 Hz, 1H), 7.94 (d, J=8.0 Hz, 1H), 7.82 (d, J=8.2 Hz, 1H), 7.67 (t, J=7.8 Hz, 1H), 7.61 (d, J=7.9 Hz, 1H), 7.45 (t, J=7.6 Hz, 1H), 6.96 (t, J=7.9 Hz, 1H), 6.83 (s, 1H); HRMS (ESI-TOF) [M+Na]⁺ calcd for $C_{22}H_{11}Cl_5N_2O_4Na$ 564.9054. found 564.9058; HPLC purity, 97.4%.

Example 2

In Vitro Anticancer Assays

The anticancer activities of the novel asymmetrical marinopyrroles described herein were evaluated against MDA-MB-468 cells (Table 1). IC$_{50}$ values are reported in μM.

TABLE 1

| Compound ID | Structure | MW | % Inhibition at 0.5, 5, 50 μM Est. IC$_{50}$ | IC$_{50}$ | Mean |
|---|---|---|---|---|---|
| Racemic Marinopyrrole A | | 510.15 | | 2.19<br>1.84<br>2.07 | 2.03 ± 0.18 |
| (+)-Marinopyrrole A | | 510.15 | | 2.14<br>1.64 | 1.88 |
| (−)-Marinopyrrole A | | 510.15 | | 3.47<br>2.87 | 3.17 |
| Compound 7 | 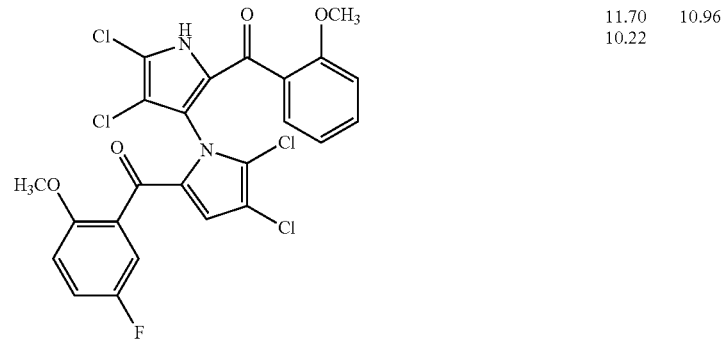 | | | 11.70<br>10.22 | 10.96 |

TABLE 1-continued

| Compound ID | Structure | MW | Est. IC$_{50}$ | % Inhibition at 0.5, 5, 50 μM IC$_{50}$ | Mean |
|---|---|---|---|---|---|
| Compound 5 | 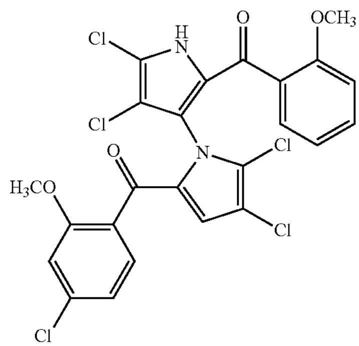 [SMILES: COc1ccccc1C(=O)c1[nH]c(Cl)c(Cl)c1-n1c(C(=O)c2ccc(Cl)cc2OC)cc(Cl)c1Cl] | | | 14.00 12.45 | 13.23 |
| Compound 8 | 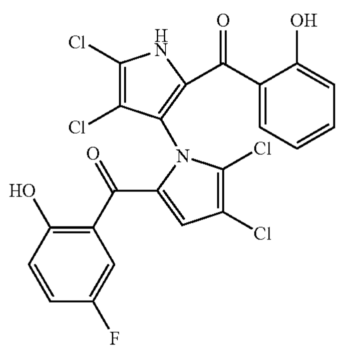 [SMILES: O=C(c1ccccc1O)c1[nH]c(Cl)c(Cl)c1-n1c(C(=O)c2cc(F)ccc2O)cc(Cl)c1Cl] | | | 2.23 2.05 | 2.14 |
| Compound 2 | 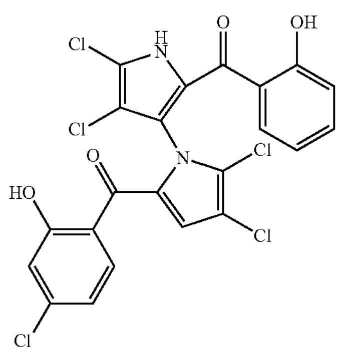 [SMILES: O=C(c1ccccc1O)c1[nH]c(Cl)c(Cl)c1-n1c(C(=O)c2ccc(Cl)cc2O)cc(Cl)c1Cl] | | | 1.72 1.17 | 1.45 |
| Compound 37 | 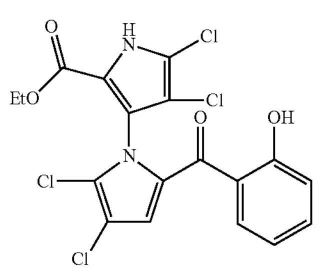 [SMILES: CCOC(=O)c1[nH]c(Cl)c(Cl)c1-n1c(C(=O)c2ccccc2O)cc(Cl)c1Cl] | 462.11 | | 15.71 | |

TABLE 1-continued

| Compound ID | Structure | MW | % Inhibition at 0.5, 5, 50 μM Est. IC$_{50}$ | IC$_{50}$ | Mean |
|---|---|---|---|---|---|
| Compound 38 | 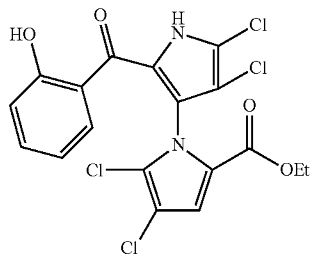 [SMILES: CCOC(=O)c1cc(Cl)c(Cl)n1-c1c(C(=O)c2ccccc2O)[nH]c(Cl)c1Cl] | 462.11 | | 2.73 1.44 | 2.09 |
| Compound 35 | 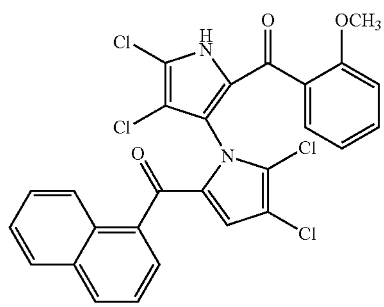 [SMILES: COc1ccccc1C(=O)c1[nH]c(Cl)c(Cl)c1-n1c(C(=O)c2cccc3ccccc23)cc(Cl)c1Cl] | | | 10.49 | |
| Compound 11 | 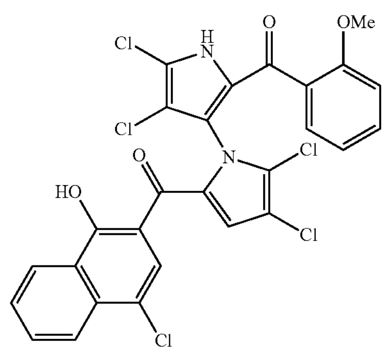 [SMILES: COc1ccccc1C(=O)c1[nH]c(Cl)c(Cl)c1-n1c(C(=O)c2cc(Cl)c3ccccc3c2O)cc(Cl)c1Cl] | | | 10.72 | |
| Compound 10 | 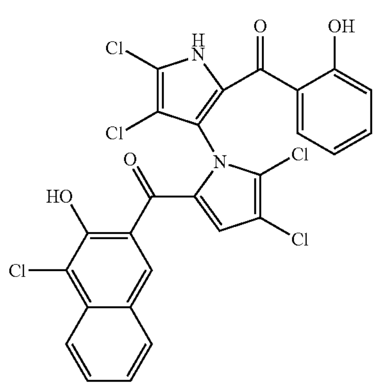 [SMILES: O=C(c1ccccc1O)c1[nH]c(Cl)c(Cl)c1-n1c(C(=O)c2cc3ccccc3c(Cl)c2O)cc(Cl)c1Cl] | | | 1.94 1.46 | 1.7 |

TABLE 1-continued

| Compound ID | Structure | MW | % Inhibition at 0.5, 5, 50 μM Est. IC$_{50}$ | IC$_{50}$ | Mean |
|---|---|---|---|---|---|
| Compound 12 | 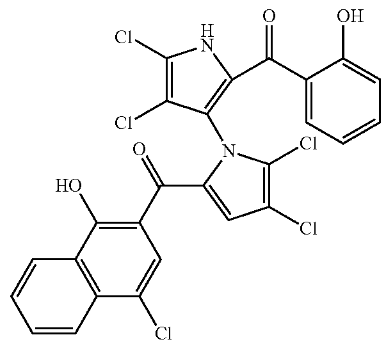 [SMILES: O=C(c1ccccc1O)c1[nH]c(Cl)c(Cl)c1-n1c(C(=O)c2cc(Cl)c3ccccc3c2O)cc(Cl)c1Cl] | | | 1.90<br>1.89 | 1.89 |
| Compound 34 | 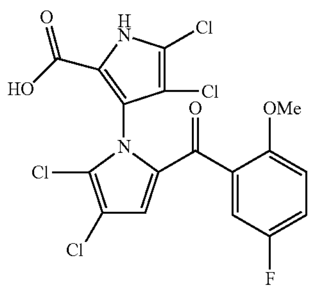 [SMILES: COc1ccc(F)cc1C(=O)c1cc(Cl)c(Cl)n1-c1c(C(=O)O)[nH]c(Cl)c1Cl] | 466.07 | | 33.52 | |
| Compound 39 | 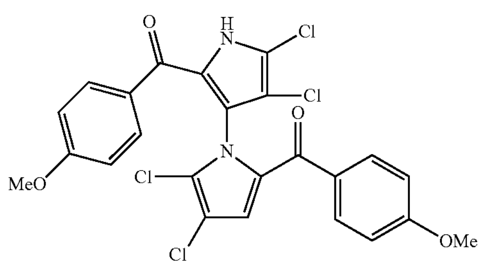 [SMILES: COc1ccc(C(=O)c2[nH]c(Cl)c(Cl)c2-n2c(C(=O)c3ccc(OC)cc3)cc(Cl)c2Cl)cc1] | 538.21 | | 18.34 | |
| Compound 9 | 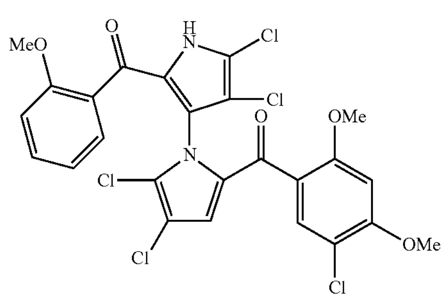 [SMILES: COc1cc(OC)c(C(=O)c2cc(Cl)c(Cl)n2-c2c(C(=O)c3ccccc3OC)[nH]c(Cl)c2Cl)cc1Cl] | 602.68 | | 20.35 | |
| Compound 21 | 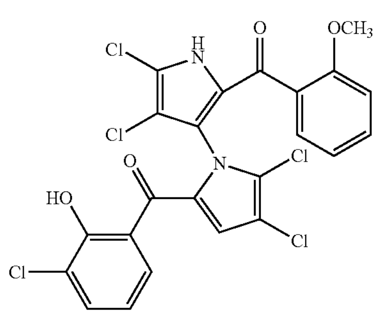 [SMILES: COc1ccccc1C(=O)c1[nH]c(Cl)c(Cl)c1-n1c(C(=O)c2cccc(Cl)c2O)cc(Cl)c1Cl] | 558.625 | −0.4<br>3.8, 14.8<br>99.1<br>25 | | |

TABLE 1-continued

| Compound ID | Structure | MW | Est. IC$_{50}$ | % Inhibition at 0.5, 5, 50 μM IC$_{50}$ | Mean |
|---|---|---|---|---|---|
| Compound 25 | 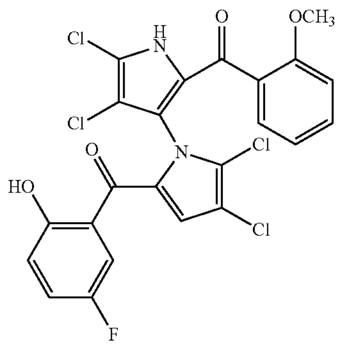 [SMILES: COc1ccccc1C(=O)c1[nH]c(Cl)c(Cl)c1-n1c(C(=O)c2cc(F)ccc2O)cc(Cl)c1Cl] | 542.171 | 2.4 | 3.6, 9.3 95.7 28 | |
| Compound 33 | 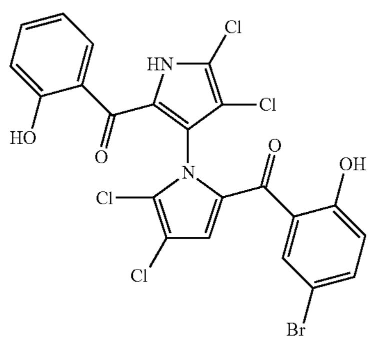 [SMILES: O=C(c1ccccc1O)c1[nH]c(Cl)c(Cl)c1-n1c(C(=O)c2cc(Br)ccc2O)cc(Cl)c1Cl] | 589.05 | 10.8 | 58.7, 99.3 2 | 3.87 |
| Compound 27 | 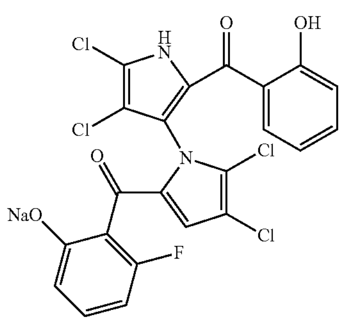 | 550.126 | 3.9 | 10.0, 26.4 96.3 25 | |
| Compound 3 | | 544.6 | 7.0 | 83.4 100 1 | 1.95 2.39 | 2.17 |

TABLE 1-continued

| Compound ID | Structure | MW | % Inhibition at 0.5, 5, 50 μM Est. IC$_{50}$ | IC$_{50}$ | Mean |
|---|---|---|---|---|---|
| Compound 1 | 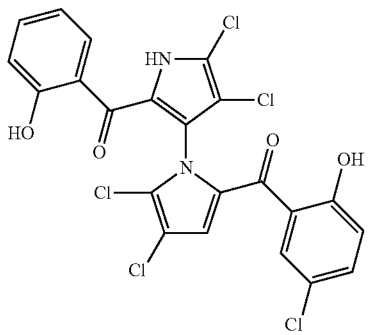 [SMILES: O=C(c1ccccc1O)c1[nH]c(Cl)c(Cl)c1-n1c(C(=O)c2cc(Cl)ccc2O)cc(Cl)c1Cl] | 544.6 | 1.6 43.6, 68.2 98.3 9 | | |
| Compound 30 | 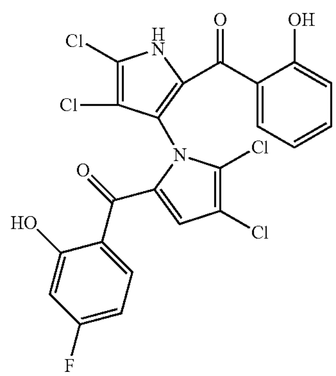 [SMILES: O=C(c1ccccc1O)c1[nH]c(Cl)c(Cl)c1-n1c(C(=O)c2ccc(F)cc2O)cc(Cl)c1Cl] | 528.144 | 10.8 78.6 94.7 1 | 0.94 1.14 | 1.04 |
| Compound 31 | 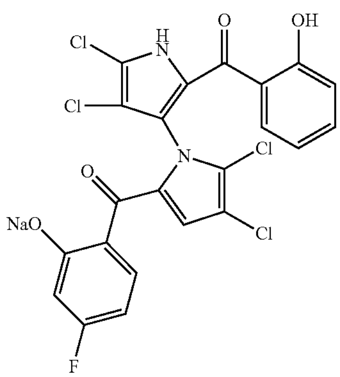 | 550.126 | 5.6 63.5 99.4 2 | 3.97 2.33 | 3.15 |
| Compound 32 | 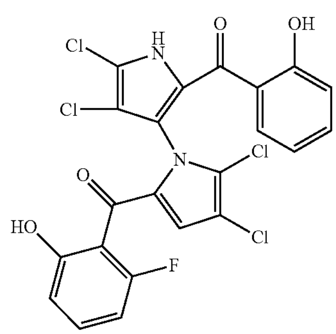 [SMILES: O=C(c1ccccc1O)c1[nH]c(Cl)c(Cl)c1-n1c(C(=O)c2c(O)cccc2F)cc(Cl)c1Cl] | 528.144 | 0 40.6, 43.1 87.7 12 | | |

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A compound of the following structure:

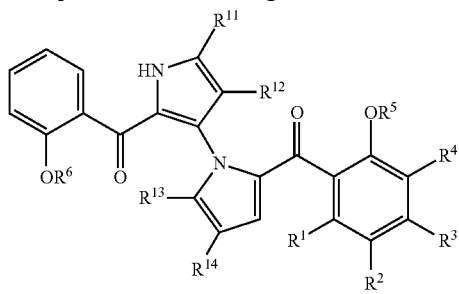

or a pharmaceutically acceptable salt or prodrug thereof, wherein:

$R^1$, $R^2$, $R^3$, and $R^4$, are each independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

each $R^{11}$, $R^{12}$, $R^{13}$, and $R^{14}$ are F, Cl, Br, or I; and $R^5$ and $R^6$ are each selected from hydrogen, substituted or unsubstituted alkyl, substituted or unsubstituted heteroalkyl, and monovalent cation, and wherein at least one of $R^3$ and $R^4$ is a halogen.

2. The compound of claim 1, wherein at least one of $R^3$ and $R^4$ is Cl.

3. The compound of claim 1, wherein $R^{11}$, $R^{12}$, $R^{13}$, and $R^{14}$ are each Cl.

4. The compound of claim 1, wherein the compound is

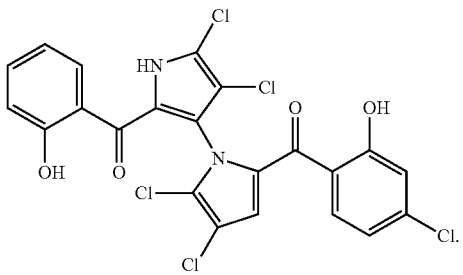 [SMILES: O=C(c1ccccc1O)c1[nH]c(Cl)c(Cl)c1-n1c(C(=O)c2ccc(Cl)cc2O)cc(Cl)c1Cl]

5. The compound of claim 1, wherein the compound is

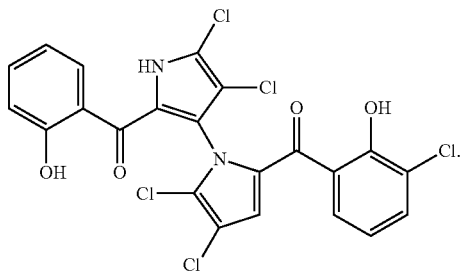 [SMILES: O=C(c1ccccc1O)c1[nH]c(Cl)c(Cl)c1-n1c(C(=O)c2cccc(Cl)c2O)cc(Cl)c1Cl]

6. The compound of claim 1, wherein the compound is:

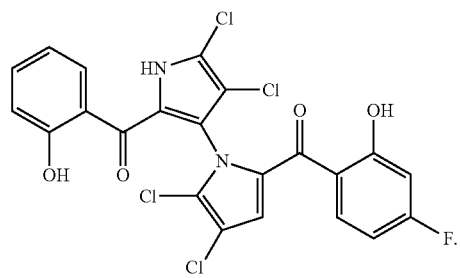 [SMILES: O=C(c1ccccc1O)c1[nH]c(Cl)c(Cl)c1-n1c(C(=O)c2ccc(F)cc2O)cc(Cl)c1Cl]

7. A compound of the following structure:

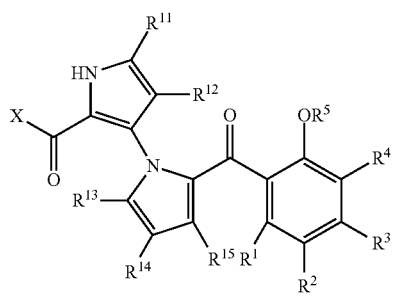

or a pharmaceutically acceptable salt or prodrug thereof, wherein:

$R^1$, $R^2$, $R^3$, $R^4$, $R^{11}$, $R^{12}$, $R^{13}$, $R^{14}$, and $R^{15}$ are each independently selected from hydrogen, halogen, hydroxyl, cyano, nitro, substituted or unsubstituted amino, substituted or unsubstituted alkyl, substituted or unsubstituted heteroalkyl, substituted or unsubstituted alkenyl, substituted or unsubstituted heteroalkenyl, substituted or unsubstituted alkynyl, substituted or unsubstituted heteroalkynyl, substituted or unsubstituted aryl, substituted or unsubstituted heteroaryl, substituted or unsubstituted alkoxyl, substituted or unsubstituted aryloxyl, and substituted or unsubstituted carboxyl;

$R^5$ is hydrogen, substituted or unsubstituted alkyl, substituted or unsubstituted heteroalkyl, substituted or unsubstituted aryl, substituted or unsubstituted heteroaryl, or a monovalent cation; and X is hydroxyl, substituted or unsubstituted alkoxyl, or substituted or unsubstituted amino, wherein if $R^1$, $R^2$, $R^3$, $R^4$, $R^5$, and $R^{15}$ are H and $R^{11}$, $R^{12}$, $R^{13}$, and $R^{14}$, are Cl, then X is other than OEt.

8. A composition, comprising a compound of claim 1 and a pharmaceutically acceptable carrier.

9. A method of treating or preventing cancer in a subject, comprising administering to the subject an effective amount of a compound of claim 1.

10. A method of treating or preventing cancer in a subject, comprising administering to the subject an effective amount of a compound selected from the group consisting of:

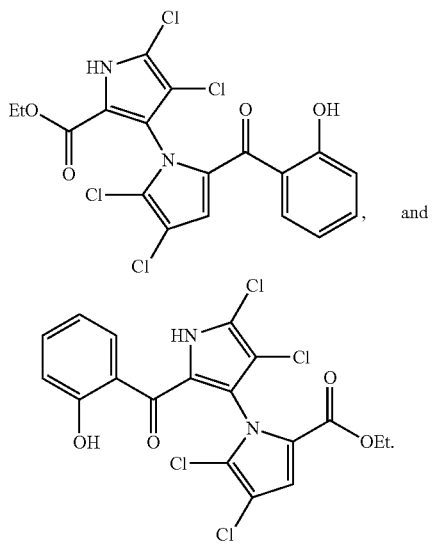

, and

11. The method of claim 9, wherein the cancer is selected from the group consisting of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer.

12. The method of claim 9, further comprising administering a second compound or composition, wherein the second compound or composition includes an anticancer agent.

13. The method of claim 9, further comprising administering an effective amount of ionizing radiation to the subject.

14. A method of killing a tumor cell in a subject, comprising:
    contacting the tumor cell with an effective amount of a compound claim 1.

15. A method of killing a tumor cell in a subject, comprising:
    contacting the tumor cell with an effective amount of a compound selected from the group consisting of:

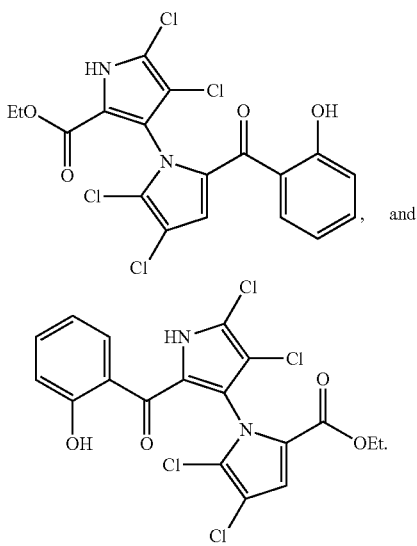

, and

16. The method of claim 14, further comprising contacting the tumor cell with a second compound or composition, wherein the second compound or composition includes an anticancer agent.

17. The method of claim 14, wherein the tumor cell is a Mcl-1 dependent cell.

18. The method of claim 14, further comprising irradiating the tumor cell with an effective amount of ionizing radiation.

19. A method of radiotherapy of a tumor, comprising:
    contacting the tumor with an effective amount of a compound or composition of claim 1; and
    irradiating the tumor with an effective amount of ionizing radiation.

* * * * *